(12) United States Patent
Zanella et al.

(10) Patent No.: US 9,289,409 B2
(45) Date of Patent: Mar. 22, 2016

(54) SULINDAC FORMULATIONS IN A BIODEGRADABLE MATERIAL

(75) Inventors: John Myers Zanella, Cordova, TN (US); Vanja M King, Memphis, TN (US); Christopher M Hobot, Tonka Bay, MN (US); S Mark Cox, Inver Grove Heights, MN (US); Danielle Biggs, Collierville, TN (US); Katara Shaw, Birmingham, AL (US); William F McKay, Memphis, TN (US); Kathy L Remsen, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1127 days.

(21) Appl. No.: 12/413,236

(22) Filed: Mar. 27, 2009

(65) Prior Publication Data

US 2009/0264531 A1 Oct. 22, 2009

Related U.S. Application Data

(60) Provisional application No. 61/046,246, filed on Apr. 18, 2008.

(51) Int. Cl.
| | |
|---|---|
| A01N 43/00 | (2006.01) |
| A61K 31/33 | (2006.01) |
| A61K 31/255 | (2006.01) |
| A61K 9/00 | (2006.01) |
| A61K 9/20 | (2006.01) |

(52) U.S. Cl.
CPC ............. *A61K 31/255* (2013.01); *A61K 9/0024* (2013.01); *A61K 9/204* (2013.01)

(58) Field of Classification Search
None
See application file for complete search history.

(56) References Cited

U.S. PATENT DOCUMENTS

| | | | |
|---|---|---|---|
| 4,624,255 A | | 11/1986 | Schenck et al. |
| 4,704,405 A | * | 11/1987 | O'Neill et al. ................. 514/568 |
| 4,863,457 A | | 9/1989 | Lee |
| 5,522,844 A | | 6/1996 | Johnson |
| 5,868,789 A | | 2/1999 | Huebner |
| 5,980,927 A | * | 11/1999 | Nelson et al. ................. 424/426 |
| 6,069,129 A | | 5/2000 | Sandberg et al. |
| 6,130,200 A | * | 10/2000 | Brodbeck et al. ............ 424/85.4 |
| 6,179,862 B1 | | 1/2001 | Sawhney |
| 6,287,588 B1 | | 9/2001 | Shih et al. |
| 6,331,311 B1 | | 12/2001 | Brodbeck et al. |
| 6,428,804 B1 | | 8/2002 | Suzuki et al. |
| 6,461,631 B1 | | 10/2002 | Dunn et al. |
| 6,589,549 B2 | | 7/2003 | Shih et al. |
| 6,630,155 B1 | | 10/2003 | Chandrashekar et al. |
| 6,632,457 B1 | | 10/2003 | Sawhney |
| 6,756,058 B2 | | 6/2004 | Brubaker et al. |
| 6,773,714 B2 | | 8/2004 | Dunn et al. |
| 6,974,462 B2 | | 12/2005 | Sater |
| 7,144,412 B2 | | 12/2006 | Wolf et al. |
| 7,166,570 B2 | | 1/2007 | Hunter et al. |
| 7,220,281 B2 | | 5/2007 | Lambrecht et al. |
| 7,229,441 B2 | | 6/2007 | Trieu et al. |
| 7,235,043 B2 | | 6/2007 | Gellman et al. |
| 7,318,840 B2 | | 1/2008 | McKay |
| 7,329,259 B2 | | 2/2008 | Cragg |
| 7,361,168 B2 | | 4/2008 | Makower et al. |
| 7,367,978 B2 | | 5/2008 | Drewry et al. |
| 2002/0009454 A1 | | 1/2002 | Boone et al. |
| 2002/0090398 A1 | | 7/2002 | Dunn et al. |
| 2003/0204191 A1 | | 10/2003 | Sater et al. |
| 2004/0072799 A1 | | 4/2004 | Li et al. |
| 2004/0082540 A1 | | 4/2004 | Hermida Ochoa |
| 2004/0109893 A1 | * | 6/2004 | Chen et al. ................... 424/468 |
| 2004/0214793 A1 | | 10/2004 | Hermida Ochoa |
| 2005/0142163 A1 | | 6/2005 | Hunter et al. |
| 2005/0186261 A1 | | 8/2005 | Avelar et al. |
| 2005/0197293 A1 | | 9/2005 | Mellis et al. |
| 2005/0245905 A1 | | 11/2005 | Schmidt et al. |
| 2006/0002979 A1 | * | 1/2006 | Ashammakhi et al. ....... 424/426 |
| 2006/0106361 A1 | | 5/2006 | Muni et al. |
| 2006/0122150 A1 | | 6/2006 | Argentieri et al. |

(Continued)

FOREIGN PATENT DOCUMENTS

| | | | | |
|---|---|---|---|---|
| WO | WO03005961 A2 | | 1/2003 | |
| WO | WO 2005/000278 | * | 1/2005 | ............... A61K 9/22 |

(Continued)

OTHER PUBLICATIONS

Al Malyan et al. in the Journal of Craniofacial Surgery 17,(2) 302-313 (2006).*
'NIH Medline' (www.nlm.nih.gov/medlineplus/druginfo/meds/a681037.html) accessed online Dec. 1, 2010.*
Moniche et al., in Anesthesiology 2002, 96, 725-741.*
Syringe Needle Gauge Chart (www.sigmaaldrich.com/ chemistry/stockroom-reagents/learning-center/technical-library/needle-gauge-chart.html.*
Santovena et al. In Biomaterials 25 (2004) 925-931.*
Shnider and Levinson's anesthesia for obstetrics 4th Edition, Eppincott, Williams and Wilkins, Philadelphia, Pa. (2202).*

(Continued)

*Primary Examiner* — Dennis Heyer
*Assistant Examiner* — Daniel M Podgorski
(74) *Attorney, Agent, or Firm* — Sorell Lenna & Schmidt LLP

(57) ABSTRACT

Effective treatments of pain and/or inflammation for extended periods of time are provided. Through the administration of an effective amount of sulindac or a pharmaceutically acceptable salt thereof at or near a target site, one can relieve pain and/or inflammation caused by diverse sources, including but not limited to spinal disc herniation (i.e. sciatica), spondilothesis, stenosis, discongenic back pain and joint pain, as well as pain that is incidental to surgery. When appropriate formulations are provided within biodegradable polymers, this relief can be continued for at least three days, at least twenty-five days. In some embodiments, the relief can be for at least fifty days, at least one hundred days, at least one hundred and thirty-five days or at least one hundred and eighty days.

23 Claims, 25 Drawing Sheets

(56) References Cited

U.S. PATENT DOCUMENTS

| | | |
|---|---|---|
| 2006/0148903 A1 | 7/2006 | Burch et al. |
| 2006/0189944 A1 | 8/2006 | Campbell et al. |
| 2006/0253100 A1* | 11/2006 | Burright et al. ............... 604/512 |
| 2007/0156180 A1 | 7/2007 | Jaax et al. |
| 2007/0185497 A1 | 8/2007 | Cauthen et al. |
| 2007/0202074 A1 | 8/2007 | Shalaby |
| 2007/0243225 A1 | 10/2007 | McKay |
| 2007/0243228 A1 | 10/2007 | McKay |
| 2008/0091207 A1 | 4/2008 | Truckai et al. |

FOREIGN PATENT DOCUMENTS

| | | |
|---|---|---|
| WO | 2006007402 A2 | 1/2006 |
| WO | 2008014066 A1 | 1/2008 |
| WO | 2008157057 A2 | 12/2008 |

OTHER PUBLICATIONS

Inherent Viscosity' in www.absorbables.com/inherent viscosity.htm.*

'Sensor One dynecm2 conversion table' in www.sensorone.co.uk/pressure-measurement-glossary/.*

Kim et al. (International Journal of Pharmaceutics, 2005, 304, 165-177).*

QLT, INC., Atrigel Drug Delivery System, www.ciltinc.com, Jul. 2006.

International Search Report and Written Opinion for International Application No. PCT/US2009/041042 mailed on Nov. 24, 2009.

Seo, S.-A. et al., "A local delivery system for fentanyl based on biodegradable poly(L-lactide-co-glycolide) oligomer". Int. J. Pharm., 2002, vol. 239, pp. 93-101. See abstract; table 1; figures 2-5; conclusion.

Tarantili P A et al: "Design of biodegradable polymer systems for drug release applications", Advanced Polymers, Composites and Technologies : Selected Contributions From the Conference in Budapest (Hungary), Sep. 13-16, 2005 Wiley-VCH, DE, pp. 1-3, XP002594563, ISBN: 978-3-527-31745-5 [retrieved on Sep. 1, 2005].

Deng J-S et al: "In vitro characterization of polyorthoester microparticles containing bupivacaine", Pharmaceutical Development and Technology, New York, NY, US, vol. 8, No. 1, Jan. 1, 2003 pp. 31-38, XP008113124, ISSN: 1083-7450, DOI: 10.1081/PDT-120017521, abstract.

International Search Report and Written Opinion for PCT/US2009/041042, the counterpart application mailed on Oct. 14, 2011, 10 pages.

* cited by examiner

| NOTEBOOK ID | POLYMER TYPE | DRUG LOAD (W: %) | EXCIPIENT | PELLET SIZE (L x Dia; mm) OR DESCRIPTION | PROCESSING |
|---|---|---|---|---|---|
| 12702-28-1 | 85/15 PLGA & Sul PARTICLES SUSPENDED IN POE GEL (13027-34) | 30 | N/A | DRUG LOADED PARTICLES IN GEL | HAND-MIX |
| 12702-28-3 | POE GEL (13027-34) | 3 | N/A | FREE DRUG SUSPENDED IN GEL | HAND-MIX |
| 12702-28-4 | POE GEL (13027-34) | 6 | N/A | FREE DRUG SUSPENDED IN GEL | HAND-MIX |
| 12702-30-1 | POE (12811-01) MICROPARTICLES POE GEL (13027-34) | 19 | N/A | DRUG LOADED MS SUSPENDED IN GEL | HAND-MIX |
| 12702-31-1 | 85/15 PLGA | 1.5 | N/A | DRUG LOADED INTO POLYMER/SOLVENT | HAND-MIX |
| 12702-31-2 | 85/15 PLGA | 3 | N/A | DRUG LOADED INTO POLYMER/SOLVENT | HAND-MIX |
| 12702-32 | POE (12811-01) MICROPARTICLES POE GEL (13027-34) | 0.4 | N/A | DRUG LOADED MS SUSPENDED IN GEL | HAND-MIX |
| 12702-36-1 | POE 12811-01 & 13027-34 | 10 | MgCO3 | DRUG LOADED PARTICLES SUSPENED IN GEL | HAND-MIX |
| 12702-36-2 | POE 12811-01 & 13027-34 | 15 | MgCO3 | DRUG LOADED PARTICLES SUSPENED IN GEL | HAND-MIX |
| 12702-36-3 | POE 12811-01 & 13027-34 | 20 | MgCO3 | DRUG LOADED PARTICLES SUSPENED IN GEL | HAND-MIX |
| 12702-38 | POE (12811-01) MICROPARTICLES POE GEL 13027-40 | 20 | MgCO3 | DRUG LOADED PARTICLES SUSPENED IN GEL | HAND-MIX |
| 12702-39 | POE 13027-34 | 0.6 | MgCO3 | FREE DRUG SUSPENDED IN GEL | HAND-MIX |
| 12702-40 | POE (12811-01) MICROPARTICLES POE 13027-32 | 20 | MgCO3 | DRUG LOADED MS SUSPENDED IN GEL | HAND-MIX |
| 12702-41 | POE (12811-01) MICROPARTICLES POE 13027-32 | 0.4 | MgCO3 | DRUG LOADED MS SUSPENDED IN GEL | HAND-MIX |
| 12702-42-1 | 75/25 PLGA | 15 | mPEG | 10 x 1.5 | SOLVENT PREP FOLLOWED BY EXTRUSION |
| 12702-49 | 50/50 PLGA | 15 | PEG | 10 x 1.5 | SOLVENT-LESS PREP FOLLOWED BY EXTRUSION |
| 12702-57-1 | 75/25 PLGA | 11 | Parafin oil | N/A; NO PRODUCT | POLYMER DISSOLVED IN NMP |
| 12702-57-2 | 75/25 PLGA | 10 | Glycerol Mono | | POLYMER DISSOLVED IN NMP |
| 12702-57-3 | 75/25 PLGA | 11 | PEG bis(ethyl hex) | | POLYMER DISSOLVED IN NMP |
| 12702-57-4 | 75/25 PLGA | 10 | | | POLYMER DISSOLVED IN NMP |
| 12702-60-1 | 75/25 PLGA | 15 | N/A | GROUND PARTICLES | SOLVENT PREP FOLLOWED BY GRINDING |
| 12702-66-1 | 75/25 PLGA-PEG 2000 | 5 | mPEG | 10 x 2 | SOLVENT PREP FOLLOWED BY EXTRUSION |
| 12702-66-2 | 75/25 PLGA-PEG 2000 | 5 | TBC-Ac | 10 x 2 | SOLVENT PREP FOLLOWED BY EXTRUSION |
| 12702-66-3 | 75/25 PLGA-PEG 6000 | 5 | mPEG | 10 x 2 | SOLVENT PREP FOLLOWED BY EXTRUSION |
| 12702-66-4 | 75/25 PLGA-PEG 6000 | 5 | TBC-Ac | 10 x 2 | SOLVENT PREP FOLLOWED BY EXTRUSION |
| 12702-66-5 | 75/25 PLGA | 5 | mPEG | 10 x 1.5 | SOLVENT PREP FOLLOWED BY EXTRUSION |
| 12702-66-6 | 75/25 PLGA | 5 | TBC-Ac | 10 x 2 | SOLVENT PREP FOLLOWED BY EXTRUSION |
| 12702-66-7 | 75/25 PLGA (HMW) | 5 | mPEG | 10 x 2 | SOLVENT PREP FOLLOWED BY EXTRUSION |
| 12702-66-8 | 75/25 PLGA (HMW) | 5 | TBC-Ac | 10 x 1.5 | SOLVENT PREP FOLLOWED BY EXTRUSION |
| 12702-68-14 | 75/25 PLGA | 2 | mPEG | 10 x 2 | SOLVENT PREP FOLLOWED BY EXTRUSION |
| 12702-72-4 | 85/15 PLGA | 5 | mPEG | 10 x 1.5 | SOLVENT PREP FOLLOWED BY EXTRUSION |
| 12702-75-1 | 85/15 PLGA | 5 | N/A | 10 x 1 | SOLVENT-LESS PREP FOLLOWED BY EXTRUSION |
| 12702-75-2 | 85/15 PLGA | 10 | N/A | 10 x 1 | SOLVENT-LESS PREP FOLLOWED BY EXTRUSION |
| 12702-75-3 | 85/15 PLGA | 5 | mPEG | 10 x 1 | SOLVENT-LESS PREP FOLLOWED BY EXTRUSION |
| 12702-75-4 | 85/15 PLGA | 10 | mPEG | 10 x 1 | SOLVENT-LESS PREP FOLLOWED BY EXTRUSION |
| 12702-75-1 | 85/15 PLGA | 5 | N/A | 10 x 1 | SOLVENT-LESS PREP FOLLOWED BY EXTRUSION |
| 12702-75-2 | 85/15 PLGA | 10 | N/A | 10 x 1 | SOLVENT-LESS PREP FOLLOWED BY EXTRUSION |
| 12702-75-3 | 85/15 PLGA | 5 | mPEG | 10 x 1 | SOLVENT-LESS PREP FOLLOWED BY EXTRUSION |
| 12702-75-4 | 85/15 PLGA | 10 | mPEG | 10 x 1 | SOLVENT-LESS PREP FOLLOWED BY EXTRUSION |
| 12702-79-1 | 85/15 PLGA | 5 | N/A | 0.8 x 0.8 | SOLVENT-LESS PREP FOLLOWED BY EXTRUSION |
| 12702-79-2 | 85/15 PLGA | 5 | N/A | 0.8 x 0.8 | SOLVENT-LESS PREP FOLLOWED BY EXTRUSION |
| 12702-79-3 | 85/15 PLGA | 5 | mPEG | 0.8 x 0.8 | SOLVENT-LESS PREP FOLLOWED BY EXTRUSION |
| 12702-79-4 | 85/15 PLGA | 5 | mPEG | 0.8 x 0.8 | SOLVENT-LESS PREP FOLLOWED BY EXTRUSION |

TABLE 2

FIG. 5

| NOTEBOOK ID | POLYMER TYPE | DRUG LOAD (Wt %) | EXCIPIENT | PELLET SIZE (L x Dia; mm) OR DESCRIPTION | PROCESSING |
|---|---|---|---|---|---|
| 12702-80-3 | 75/25 PLGA | 5 | mPEG | 1.0 x 1.0 | SOLVENT-LESS PREP FOLLOWED BY EXTRUSION |
| 12702-80-4 | 75/25 PLGA | 10 | mPEG | 1.0 x 1.0 | SOLVENT-LESS PREP FOLLOWED BY EXTRUSION |
| 12702-80-5 | 75/25 PLGA | 15 | mPEG | 1.0 x 1.0 | SOLVENT-LESS PREP FOLLOWED BY EXTRUSION |
| 12702-80-6 | 85/15 PLGA | 15 | mPEG | 1.0 x 1.0 | SOLVENT-LESS PREP FOLLOWED BY EXTRUSION |
| 12702-100-1 | 85/15 PLGA | 15 | mPEG | 0.7 x 0.7 | SOLVENT-LESS PREP FOLLOWED BY EXTRUSION |
| 12702-100-2 | 85/15 PLGA | 20 | mPEG | 0.7 x 0.7 | SOLVENT-LESS PREP FOLLOWED BY EXTRUSION |
| 12702-100-3 | 85/15 PLGA | 25 | mPEG | 0.7 x 0.7 | SOLVENT-LESS PREP FOLLOWED BY EXTRUSION |
| 12702-100-4 | 85/15 PLGA | 30 | mPEG | 0.7 x 0.7 | SOLVENT-LESS PREP FOLLOWED BY EXTRUSION |
| 12702-100-5 | 90/10 PLGA | 15 | mPEG | 0.7 x 0.7 | SOLVENT-LESS PREP FOLLOWED BY EXTRUSION |
| 12702-100-6 | 90/10 PLGA | 20 | mPEG | 0.7 x 0.7 | SOLVENT-LESS PREP FOLLOWED BY EXTRUSION |
| 12702-100-7 | 90/10 PLGA | 25 | mPEG | 0.7 x 0.7 | SOLVENT-LESS PREP FOLLOWED BY EXTRUSION |
| 12702-100-8 | 90/10 PLGA | 30 | mPEG | 0.7 x 0.7 | SOLVENT-LESS PREP FOLLOWED BY EXTRUSION |
| 12702-100-9 | DL-PLA | 15 | mPEG | 0.7 x 0.7 | SOLVENT-LESS PREP FOLLOWED BY EXTRUSION |
| 12702-100-10 | DL-PLA | 20 | mPEG | 0.7 x 0.7 | SOLVENT-LESS PREP FOLLOWED BY EXTRUSION |
| 12702-100-11 | DL-PLA | 25 | mPEG | 0.7 x 0.7 | SOLVENT-LESS PREP FOLLOWED BY EXTRUSION |
| 12702-100-12 | DL-PLA | 30 | mPEG | 0.7 x 0.7 | SOLVENT-LESS PREP FOLLOWED BY EXTRUSION |
| 13395-1 | 85/15 PLGA | 20 | PEG | 0.8 x 0.8 | SOLVENT-LESS PREP FOLLOWED BY EXTRUSION |
| 13395-2-1 | 75/25 PLGA | 15 | mPEG | 0.7 x 0.7 | SOLVENT-LESS PREP FOLLOWED BY EXTRUSION |
| 13395-2-2 | 75/25 PLGA | 20 | mPEG | 0.7 x 0.7 | SOLVENT-LESS PREP FOLLOWED BY EXTRUSION |
| 13395-2-3 | 75/25 PLGA | 25 | mPEG | 0.7 x 0.7 | SOLVENT-LESS PREP FOLLOWED BY EXTRUSION |
| 13395-2-4 | 75/25 PLGA | 30 | mPEG | 0.7 x 0.7 | SOLVENT-LESS PREP FOLLOWED BY EXTRUSION |
| 13395-27-6 | 85/15 PLGA | 25 | mPEG | 0.7 x 0.7 | SOLVENT-LESS PREP FOLLOWED BY EXTRUSION |
| 13395-27-7 | 85/15 PLGA | 30 | mPEG | 0.7 x 0.7 | SOLVENT-LESS PREP FOLLOWED BY EXTRUSION |
| 13395-27-8 | 85/15 PLGA | 15 | mPEG | 0.7 x 0.7 | SOLVENT-LESS PREP FOLLOWED BY EXTRUSION |
| 13395-27-9 | 85/15 PLGA | 20 | mPEG | 0.7 x 0.7 | SOLVENT-LESS PREP FOLLOWED BY EXTRUSION |
| 13395-27-11 | 85/15 PLGA | 25 | BaSO4;mPEG | 0.7 x 0.7 | SOLVENT-LESS PREP FOLLOWED BY EXTRUSION |
| 13395-27-13 | 90/10 PLGA | 20 | mPEG | 0.7 x 0.7 | SOLVENT-LESS PREP FOLLOWED BY EXTRUSION |
| 13395-27-14 | 90/10 PLGA | 25 | mPEG | 0.7 x 0.7 | SOLVENT-LESS PREP FOLLOWED BY EXTRUSION |
| 13395-27-15 | DL-PLA | 25 | mPEG | 0.7 x 0.7 | SOLVENT-LESS PREP FOLLOWED BY EXTRUSION |
| 13395-27-16 | DL-PLA | 30 | mPEG | 0.7 x 0.7 | SOLVENT-LESS PREP FOLLOWED BY EXTRUSION |
| 13395-31-1 | 85/15 PLGA | 25 | mPEG | 0.75 x 0.75 | SOLVENT-LESS PREP FOLLOWED BY EXTRUSION |
| 13395-31-2 | 85/15 PLGA | 25 | mPEG | 0.75 x 0.75 | SOLVENT-LESS PREP FOLLOWED BY EXTRUSION |
| 13395-31-3 | 85/15 PLGA | 25 | mPEG | 0.75 x 0.75 | SOLVENT-LESS PREP FOLLOWED BY EXTRUSION |
| 13395-31-4 | 85/15 PLGA | 30 | mPEG | 0.75 x 0.75 | SOLVENT-LESS PREP FOLLOWED BY EXTRUSION |
| 13395-31-5 | 85/15 PLGA | 30 | mPEG | 0.75 x 0.75 | SOLVENT-LESS PREP FOLLOWED BY EXTRUSION |
| 13395-31-6 | 85/15 PLGA | 30 | mPEG | 0.75 x 0.75 | SOLVENT-LESS PREP FOLLOWED BY EXTRUSION |
| 13395-35-1 | 85/15 PLGA | 25 | BaSO4;mPEG | 0.7 x 0.7 | SOLVENT-LESS PREP FOLLOWED BY EXTRUSION |
| 13395-36-1 | 85/15 PLGA | | mPEG | 0.7 x 0.7 | SOLVENT-LESS PREP FOLLOWED BY EXTRUSION |
| 13395-41-1 | 85/15 PLGA | 40 | N/A | 4 x 0.7 | SOLVENT-LESS PREP FOLLOWED BY EXTRUSION |
| 13395-58-1 | 85/15 PLGA | 20 | mPEG | 4 x 0.7 | SOLVENT-LESS PREP FOLLOWED BY EXTRUSION |
| 13395-58-2 | 85/15 PLGA | 27 | mPEG | 4 x 0.7 | SOLVENT-LESS PREP FOLLOWED BY EXTRUSION |
| 13395-58-3 | DL-PLA | 25 | mPEG | 4 x 0.7 | SOLVENT-LESS PREP FOLLOWED BY EXTRUSION |
| 13395-61-1 | 85/15 PLGA | 20 | N/A | 4 x 0.7 | SOLVENT-LESS PREP FOLLOWED BY EXTRUSION |
| 13395-61-2 | 85/15 PLGA | 27 | N/A | 4 x 0.7 | SOLVENT-LESS PREP FOLLOWED BY EXTRUSION |
| 13395-61-3 | DL-PLA | 25 | N/A | 4 x 0.7 | SOLVENT-LESS PREP FOLLOWED BY EXTRUSION |
| 13395-63-1 | 85/15 PLGA | 20 | mPEG | 4 x 0.7 | SOLVENT-LESS PREP FOLLOWED BY EXTRUSION |
| 13395-63-5 | 85/15 PLGA | 20 | mPEG | 4 x 0.7 | SOLVENT-LESS PREP FOLLOWED BY EXTRUSION |
| 13395-68-1 | DL-PLA | 25 | mPEG | 4 x 0.7 | SOLVENT-LESS PREP FOLLOWED BY EXTRUSION |
| 13395-68-2 | DL-PLA | 25 | N/A | 4 x 0.7 | SOLVENT-LESS PREP FOLLOWED BY EXTRUSION |

TABLE 2 (CONTINUED)

*FIG. 6*

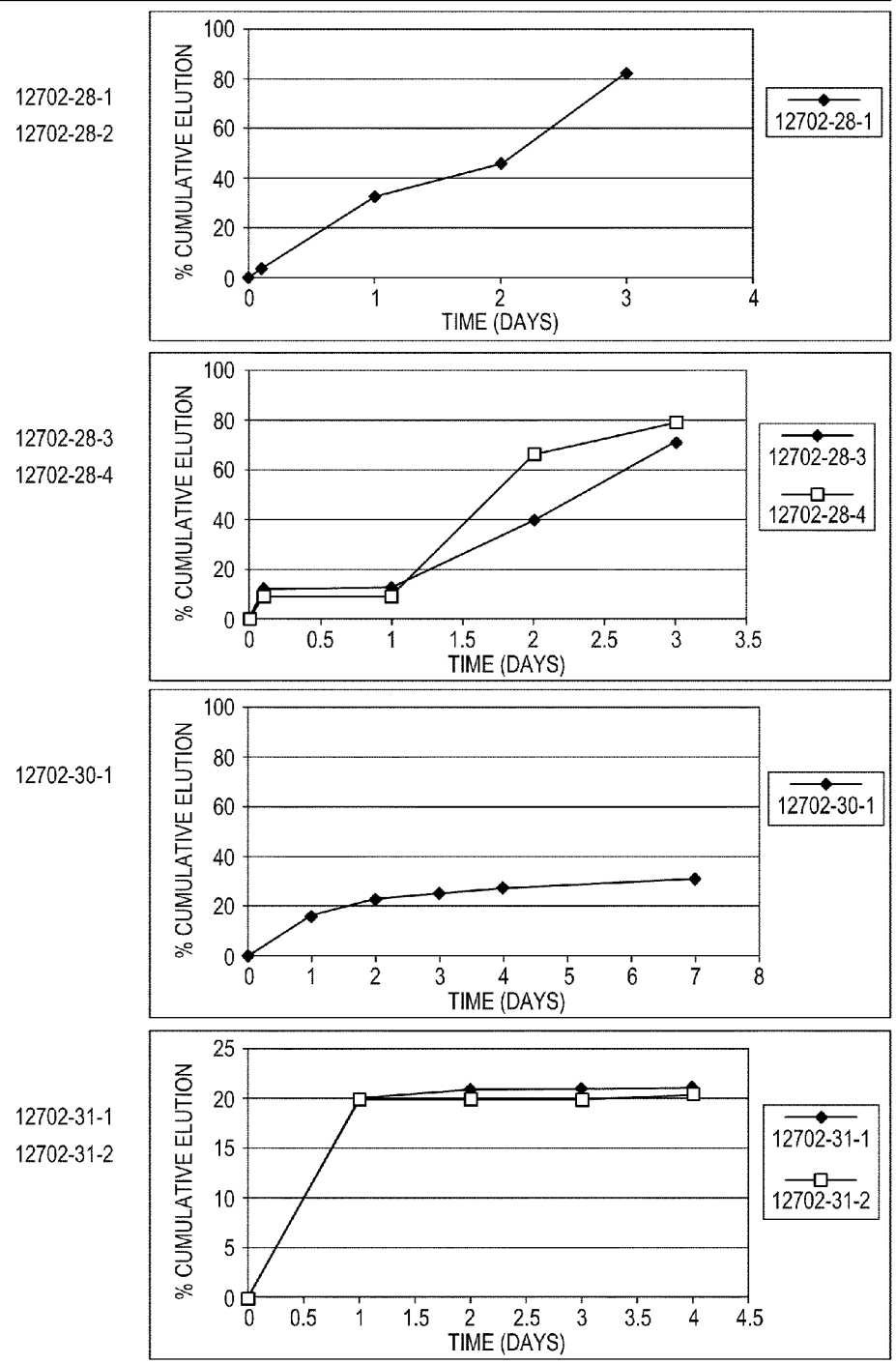

SULINDAC FORMULATIONS IN A BIODEGRADABLE MATERIAL

This application claims the benefit of the filing date of U.S. Provisional Patent Application No. 61/046,246, filed Apr. 18, 2008, entitled "Sulindac Formulations In A Biodegradable Material." U.S. Provisional Patent Application No. 61/046,246 is hereby incorporated by reference into the present disclosure.

BACKGROUND

Pain can adversely affect patients in many different ways. It can keep the patient from being active, sleeping well, enjoying family and friends, and from eating. Pain can make the patient feel afraid or depressed and prevent full participation in general rehabilitation programs and may even slow recovery.

Proper pain control is of prime importance to anyone treating many different diseases or conditions. Proper pain relief imparts significant physiological and psychological benefits to the patient. Not only does effective pain relief mean a smoother more pleasant recovery (e.g., mood, sleep, quality of life, etc.) with earlier discharge from medical/surgical/outpatient facilities, but it may also reduce the onset of chronic pain syndromes (e.g., fibromyalgia, myalgia, etc.).

Pain serves the important biological function of signaling the presence of damage or disease within the body and is often accompanied by inflammation (redness, swelling, and/or burning). There are two categories of pain: acute pain and neuropathic pain. Acute pain refers to pain experienced when tissue is being damaged or is damaged. Acute pain serves at least two physiologically advantageous purposes. First, it warns of dangerous environmental stimuli (such as hot or sharp objects) by triggering reflexive responses that end contact with the dangerous stimuli. Second, if reflexive responses do not avoid dangerous environmental stimuli effectively, or tissue injury or infection otherwise results, acute pain facilitates recuperative behaviors. For example, acute pain associated with an injury or infection encourages an organism to protect the compromised area from further insult or use while the injury or infection heals. Once the dangerous environmental stimulus is removed, or the injury or infection has resolved, acute pain, having served its physiological purpose, ends. As contrasted to acute pain, in general, neuropathic pain serves no beneficial purpose. Neuropathic pain results when pain associated with an injury or infection continues in an area once the injury or infection has resolved.

There are many painful disease or conditions that require proper pain and/or inflammation control, including but not limited to rheumatoid arthritis, osteoarthritis, a spinal disc herniation (i.e., sciatica), carpal/tarsal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, spondilothesis, stenosis, discogenic back pain, and joint pain or the like.

One particularly painful disease is sciatica. Sciatica is a chronic disease that often can be very debilitating and may take a terrible toll on those with the disease as well as their families, friends and caregivers. Sciatica is a very painful disease associated with the sciatic nerve which runs from the lower part of the spinal cord (the lumbar region), down the back of the leg and to the foot. Sciatica generally begins with a herniated disc, which later leads to local immune system activation. The herniated disc also may damage the nerve root by pinching or compressing it, leading to additional immune system activation in the area. There has been considerable interest in developing effective treatments for this painful disease, yet to date current treatments of sciatica are only partially effective.

Another particularly painful disease is spinal stenosis, where there is progressive constriction of the spinal canal and as it narrows, the nerve elements that reside within it become progressively more crowded. Eventually, the canal dimensions become sufficiently small-so as to significantly compress the nerve elements and produce pain, weakness, sensory changes, clumsiness and other manifestation of nervous system dysfunction. The disease causes lower back pain, lower extremity pain, lower extremity weakness, limitation of mobility and the high disability rates that often afflict the elderly.

Spondylolisthesis is another painful disease. Spondylolisthesis is a displacement disorder of the lumbar or cervical spine, in which one vertebral body is forwardly displaced over another vertebral body. Spondylolisthesis may be caused by a traumatic event or by degeneration of the spine. At times, the displacement disorder is accompanied by or caused by a fracture or partial collapse of one or more vertebrae or degeneration of a disc in the spine. Patients who suffer from such conditions can experience moderate to severe distortion of the thoracic skeletal structure, diminished ability to bear loads, loss of mobility, extreme and debilitating pain, and oftentimes suffer neurological deficits in nerve function One known class of pharmaceuticals to treat pain is opiods. This class of compounds is well-recognized as being among the most effective type of drugs for controlling pain. Unfortunately, because opiods are administered systemically, the associated side effects raise significant concerns, including disabling the patient, depressing the respiratory system, constipation, and psychoactive effects such as sedation and euphoria, thereby instituting a hurdle to recovery and regained mobility. Further, because of these side-effects, physicians typically limit the administration of opiods to within the first 24 hours post-surgery. Thus, there has been a considerable interest in using non-narcotic drugs that deliver direct, localized pain control at a target tissue site.

One pharmaceutical that is known to the medical profession is sulindac, (commercially available as Clinoril® from Sigma as a free acid) which is widely recognized as a non-steroidal anti-inflammatory of the arylalkanoic acid class. It may be represented by the following chemical formula $C_{20}H_{17}FO_3S$. Sulindac is a prodrug, derived from sulfinylindene that is converted in the body to an active NSAID (non-steroidal anti-inflammatory agent). More specifically, the agent is converted by liver enzymes to a sulfide that is excreted in the bile and then reabsorbed from the intestine. This is thought to help maintain constant blood levels with reduced gastrointestinal side effects.

However, to date sulindac has not been appreciated as an effective treatment for pain and/or inflammation in sustained release formulations that provide relief over at least 3 days. Thus, there is a need to develop effective formulations of this compound for this application.

SUMMARY

Compositions and methods are provided comprising sulindac or its pharmaceutically acceptable salts that are administered in order to treat pain and/or inflammation. When appropriate formulations are provided within biodegradable polymers, this relief can be continued for at least three days, at least twenty-five days. In some embodiments, the relief can be for at least fifty days, at least one hundred days, at least one hundred and thirty-five days or at least one hundred and eighty days.

According to one embodiment, there is a pharmaceutical formulation comprising: sulindac, wherein the sulindac comprises from about 20 wt. % to about 40 wt. % of the formulation, and at least one biodegradable polymer. The pharmaceutical composition may for example, be part of a drug depot. The drug depot may: (i) consist of only the sulindac (or one or more of its pharmaceutically acceptable salts) and the biodegradable polymer(s); or (ii) consist essentially of the sulindac (or one or more of its pharmaceutically acceptable salts) and the biodegradable polymer(s); or (iii) comprise the sulindac (or one or more of its pharmaceutically acceptable salts), the biodegradable polymer(s) and one or more other active ingredients, surfactants, excipients or other ingredients or combinations thereof. When there are other active ingredients, surfactants, excipients or other ingredients or combinations thereof in the formulation, in some embodiments these other compounds or combinations thereof comprise less than 20 wt. %, less than 16 wt. %, less than 15 wt. %, less than 14 wt. %, less than 13 wt. %, less than 12 wt. %, less than 11 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. %, less than 1 wt. % or less than 0.5 wt. % of the drug depot.

According to another embodiment, there is a pharmaceutical formulation comprising: sulindac, wherein the sulindac comprises from about 20 wt. % to about 40 wt. % of the formulation, and at least one biodegradable polymer, wherein the at least one biodegradable polymer comprises poly(lactic-co-glycolic acid) or poly(orthoester) or a combination thereof, and said at least one biodegradable polymer comprises at least 80 wt. % of said formulation.

According to another embodiment, there is an implantable drug depot for reducing, preventing or treating pain and/or inflammation in a patient in need of such treatment, the implantable drug depot comprising a sulindac in an amount from about 20 wt. % to about 40 wt. % of the formulation, and at least one biodegradable polymer.

According to another embodiment, there is an implantable drug depot for reducing, preventing or treating pain and/or inflammation in a patient in need of such treatment, the implantable drug depot comprising sulindac in an amount of from about 20 wt. % to about 40 wt. % of the drug depot, and at least one biodegradable polymer, wherein the at least one biodegradable polymer comprises poly(lactic-co-glycolic acid) or poly(orthoester) or a combination thereof, and said at least one biodegradable polymer comprises at least 80 wt. % of said formulation.

According to another embodiment, there is an implantable drug depot for reducing, preventing or treating pain and/or inflammation in a patient in need of such treatment, the implantable drug depot comprising sulindac in an amount of from about 20 wt. % to about 40 wt. % of the drug depot, and at least one polymer, wherein the at least one biodegradable polymer comprises poly(lactic-co-glycolic acid), poly (orthoester), polylactide, polyglycolide, D-lactide, L-lactide, D,L-lactide, D,L-lactide-caprolactone, or D, L-lactide-glycolide-caprolactone, glycolide-caprolactone, D,L-lactide-ε-caprolactone, D,L-lactide-glycolide-ε-caprolactone or a combination thereof.

According to another embodiment there is a method for treating pain and/or inflammation, wherein said method comprises implanting a drug depot in an organism (e.g., a mammal) to reduce, prevent or treat pain and/or inflammation, wherein said drug depot comprises sulindac in an amount from about 20 wt. % to about 40 wt. % of the drug depot, and at least one biodegradable polymer.

According to another embodiment, there is a method for treating acute pain and/or inflammation, wherein said method comprises: administering a pharmaceutical composition comprising sulindac and at least one biodegradable polymer to an organism, wherein said sulindac comprises from about 20 wt. % to about 40 wt. % of the drug depot.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

FIGS. 5 and 6 shows a set of exemplary sulindac formulations.

FIGS. 7-18 show in vitro elution profiles for exemplary sulindac formulations.

Figure 1:
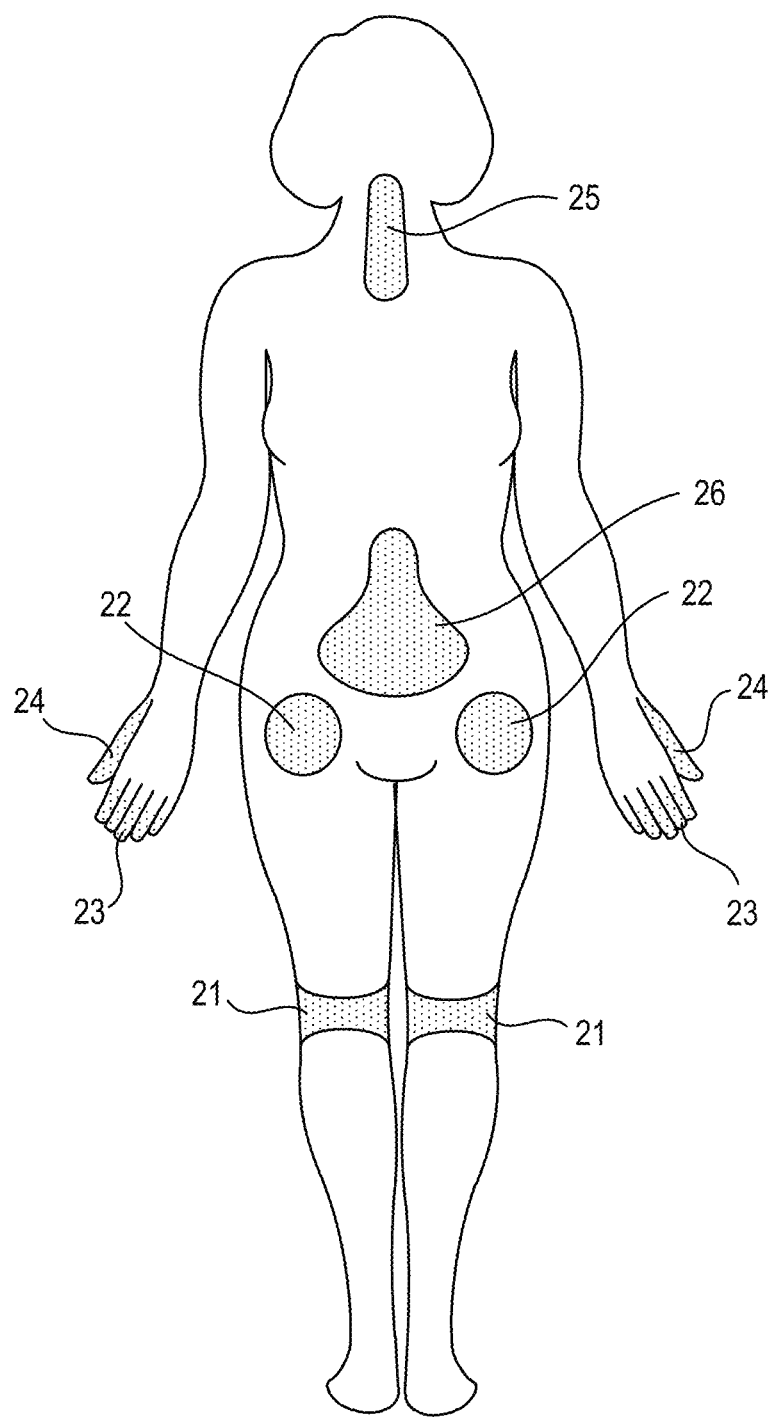
FIG. 1 illustrates a number of common locations within a patient that may be sites at which pain takes place and locations at which a drug depot containing sulindac can locally be administered thereto.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Definitions

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

A "drug depot" is the composition in which the sulindac is administered to the body. Thus, a drug depot may comprise a physical structure to facilitate implantation and retention in a desired site (e.g., a disc space, a spinal canal, a tissue of the patient, particularly at or near a site of surgery, etc.). The drug depot also comprises the drug itself.

The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 1 cm, up to about 5 cm or up to about 10 cm from the target site, and comprises sulindac. In some embodiments the therapeutic agent is placed at least 1 cm from the target site.

A "therapeutically effective amount" or "effective amount" is such that when administered, the drug results in alteration of the biological activity, such as, for example, inhibition of inflammation, reduction or alleviation of pain and/or inflammation or spasticity, improvement in the condition through muscle relaxation, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the formulation is designed for immediate release. In other embodiments the formulation is designed for sustained release. In other embodiments, the formulation comprises one or more immediate release surfaces and one or more sustained release surfaces.

A "depot" includes but is not limited to capsules, microspheres, microparticles, microcapsules, microfibers particles, nanospheres, nanoparticles, coating, matrices, wafers, pills, pellets, emulsions, liposomes, micelles, gels, or other pharmaceutical delivery compositions or a combination thereof. The drug depot may comprise a pump that holds and administers the pharmaceutical. In some embodiments, the drug depot has pores that allow release of the drug from the depot. The drug depot will allow fluid in the depot to displace the drug. However, cell infiltration into the depot will be prevented by the size of the pores of the depot. In this way, in some embodiments, the depot should not function as a tissue scaffold and allow tissue growth. Rather, the drug depot will solely be utilized for drug delivery. In some embodiments, the pores in the drug depot will be less than 250 to 500 microns. This pore size will prevent cells from infiltrating the drug depot and laying down scaffolding cells. Thus, in this embodiment, drug will elute from the drug depot as fluid enters the drug depot, but cells will be prevented from entering. In some embodiments, where there are little or no pores, the drug will elute out from the drug depot by the action of enzymes, by hydrolytic action and/or by other similar mechanisms in the human body.

Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

The term "biodegradable" includes that all or parts of the drug depot will degrade over time by the action of enzymes, by hydrolytic action and/or by other similar mechanisms in the human body. In various embodiments, "biodegradable" includes that the depot (e.g., microparticle, microsphere, etc.) can break down or degrade within the body to non-toxic components after or while a therapeutic agent has been or is being released. By "bioerodible" it is meant that the depot will erode or degrade over time due, at least in part, to contact with substances found in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

The phrases "sustained release" and "sustain release" (also referred to as extended release or controlled release) are used interchangeably herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the drug depot, or a matrix or component thereof, or as the result of metabolic transformation or dissolution of the therapeutic agent(s) or conjugates of therapeutic agent(s).

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug. The two types of formulations (sustain release and immediate release) may be used in conjunction. The sustained release and immediate release formulations may be in or more of the same depots. In various embodiments, the sustained release and immediate release formulations may be part of separate depots. For example a bolus or immediate release formulation of sulindac may be placed at or near the target site and a sustain release formulation may also be placed at or near the same site. Thus, even after the bolus becomes completely accessible, the sustain release formulation would continue to provide the active ingredient for the intended tissue.

The phrases "initial burst," "burst effect," and "bolus dose" are used interchangeably herein and refer to the release of therapeutic agent from the depot during the first 72 hours after the depot comes in contact with an aqueous fluid (e.g., synovial fluid, cerebral spinal fluid, etc.). The "burst effect" is believed to be due to the increased release of therapeutic agent from the depot. In various embodiments, the drug depot can be designed to cause an initial burst dose of therapeutic agent within the first 72 hours after implantation. In alternative embodiments, the depot (e.g., gel) is designed to avoid this initial burst effect.

The terms "treating" and "treatment" of a disease or condition refer to executing a protocol that may include administering one or more drugs to a patient (human, other normal or otherwise or other mammal), in an effort to alleviate signs or symptoms of the disease or condition. Alleviation can occur prior to signs or symptoms of the disease or condition appearing, as well as after their appearance. The terms "treating" and "treatment" include "preventing" or "prevention" of disease or undesirable condition. In addition, "treating" or "treatment" does not require complete alleviation of signs or symptoms, does not require a cure, and specifically includes protocols that have only a marginal effect on the patient. "Reducing pain" includes a decrease in pain and does not require complete alleviation of pain signs or symptoms, and does not require a cure. In various embodiments, reducing pain includes even a marginal decrease in pain. By way of example, the administration of one or more effective dosages of the sulindac may be used to prevent, treat or relieve the symptoms of pain and/or inflammation from sciatica, spondilothesis, stenosis, or the like.

"Localized" delivery includes delivery where one or more drugs are deposited within a tissue, for example, a nerve root of the nervous system or a region of the brain, or in close proximity (within about 10 cm, or preferably within about 5 cm, for example) thereto.

The term "mammal" refers to organisms from the taxonomy class "mammalian," including but not limited to humans, other primates such as chimpanzees, apes, orangutans and monkeys, rats, mice, cats, dogs, cows, horses, etc.

The phrase "pain management medication" includes one or more therapeutic agents that are administered to prevent, alleviate or remove pain entirely. These include anti-inflammatory agents, muscle relaxants, analgesics, anesthetics, narcotics, and so forth, and combinations thereof.

The phrase "release rate profile" refers to the percentage of active ingredient that is released over fixed units of time, e.g., mg/hr, mg/day, 10% per day for ten days, etc. As persons of ordinary skill know, a release rate profile may be but need not be linear. By way of a non-limiting example, the drug depot may be a pellet that releases the sulindac over a period of time.

The term "solid" is intended to mean a rigid material, while, "semi-solid" is intended to mean a material that has some degree of flexibility, thereby allowing the depot to bend and conform to the surrounding tissue requirements.

The phrase "targeted delivery system" refers to a system that provides delivery of one or more drugs depots, gels or depots dispersed in the gel having a quantity of therapeutic agent that can be deposited at or near the target site as needed for treatment of pain, inflammation or other disease or condition.

The abbreviation "DLG" refers to poly(DL-lactide-co-glycolide).

The abbreviation "DL" refers to poly(DL-lactide).

The abbreviation "LG" refers to poly(L-lactide-co-glycolide).

The abbreviation "CL" refers to polycaprolactone.

The abbreviation "DLCL" refers to poly(DL-lactide-co-caprolactone).

The abbreviation "LCL" refers to poly(L-lactide-co-caprolactone).

The abbreviation "PGA" refers to polyglycolide.

The abbreviation "PEG" refers to poly(ethylene glycol).

The abbreviation "PLGA" refers to poly(lactide-co-glycolide).

The abbreviation "PLA" refers to polylactide.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Sulindac

When referring to sulindac, unless otherwise specified or apparent from context it is understood that the inventors are also referring to pharmaceutically acceptable salts, pharmacologically-active derivatives of the sulindac or an active metabolite of the sulindac. As used herein, "pharmaceutically acceptable salts" refer to derivatives of the disclosed compounds (e.g., esters or amines) wherein the parent compound may be modified by making acidic or basic salts thereof. Examples of pharmaceutically acceptable salts include, but are not limited to, mineral or organic acid salts of basic residues such as amines; alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, or nitric acids; or the salts prepared from organic acids such as acetic, fuoric, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic acid. Pharmaceutically acceptable also includes the racemic mixtures ((+)-R and (−)-S enantiomers) or each of the dextro and levo isomers of the sulindac individually. The sulindac may be in the free acid or base form or be pegylated for long acting activity.

One well-known commercially available salt for sulindac is its sodium salt (e.g., available from Spectrum Chemical) or sulfide salt.

The sulindac or its pharmaceutically acceptable salt may be administered with a muscle relaxant. Exemplary muscle relaxants include by way of example and not limitation, alcuronium chloride, atracurium bescylate, baclofen, carbamate, carbolonium, carisoprodol, chlorphenesin, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The drug depot may comprise other therapeutic agents in addition to the sulindac as well. Therapeutic agents, in various embodiments, block the transcription or translation of TNF-α or other proteins in the inflammation cascade. Suitable therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents include IL-1 inhibitors, such Kineret® (anakinra), which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), bone morphogenetic protein (BMP) type 2 and BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), and may be useful as therapeutic agents for reducing inflammation. It is contemplated that where desirable a pegylated form of the above may be used. Examples of other therapeutic agents include NF kappa B inhibitors such as glucocorticoids, antioxidants, such as dithiocarbamate, and other compounds, such as, for example, sulfasalazine, clonidine, and/or bupivacaine.

Examples of therapeutic agents suitable for use also include, but are not limited to an anti-inflammatory agent, analgesic agent, or osteoinductive growth factor or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[-4-[C2-pyridinylamino)sulfonyl]azo]benzoic acid, tepoxalin, or tolmetin, as well as antioxidants, such as dithiocarbamate, steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

Suitable analgesic agents include, but are not limited to, acetaminophen, bupivicaine, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

Other therapeutic agents that may be included in the sulindac depot include alpha receptor agonists (e.g., alpha-1 or alpha-2 receptor agonist or combinations thereof). Examples of alpha-1 adrenergic receptor agonists include, but are in no way limited to methoxamine, methylnorepinephrine, norepinephrine, metaraminol, oxymetazoline, phenylephrine, 2-(anilinomethyl)imidazolines, synephrine, or a combination thereof.

In some embodiments, the alpha adrenergic receptor agonist comprises an alpha-2 adrenergic receptor agonist, which acts as an analgesic and/or anti-inflammatory agent. Examples of alpha-2 adrenergic receptor agonists useful in the present application include, but are in no way limited to L-norepinephrine, clonidine, dexmetdetomidine, apraclonidine, methyldopa, tizanidine, brimonidine, xylometazoline, tetrahydrozoline, oxymetazoline, guanfacine, guanabenz, guanoxabenz, guanethidine, xylazine, moxonidine, mivazerol, rilmenidine, UK 14,304, B-HT 933, B-HT 920, octopamine or a combination thereof.

Other alpha adrenergic agonists include, but are not limited to, amidephrine, amitraz, anisodamine, apraclonidine, cirazoline, detomidine, epinephrine, ergotamine, etilefrine, indanidine, lofexidine, medetomidine, mephentermine, metaraminol, methoxamine, midodrine, naphazoline, norepinephrine, norfenefrine, octopamine, oxymetazoline, phenylpropanolamine, rilmenidine, romifidine, synephrine, talipexole, tizanidine, or a combination thereof.

The sulindac may also be administered with non-active ingredients. These non-active ingredients may have multi-functional purposes including the carrying, stabilizing and controlling the release of the therapeutic agent(s). The sustained release process, for example, may be by a solution-diffusion mechanism or it may be governed by an erosion-sustained process. Typically, the depot will be a solid or semi-solid formulation comprised of a biocompatible material that can be biodegradable.

In various embodiments, the non-active ingredients will be durable within the tissue site for a period of time equal to (for biodegradable components) or greater than (for non-biodegradable components) the planned period of drug delivery. For example, the depot material may have a melting point or glass transition temperature close to or higher than body temperature, but lower than the decomposition or degradation temperature of the therapeutic agent. However, the pre-determined erosion of the depot material can also be used to provide for slow release of the loaded therapeutic agent(s).

In some embodiments, the drug depot may not be biodegradable. For example, the drug depot may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. Typically, these types of drug depots may need to be removed.

In some instances, it may be desirable to avoid having to remove the drug depot after use. In those instances, the depot may comprise a biodegradable material. There are numerous materials available for this purpose and having the characteristic of being able to breakdown or disintegrate over a prolonged period of time when positioned at or near the target tissue. As a function of the chemistry of the biodegradable material, the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

In various embodiments, the depot may comprise a bioabsorbable, a bioabsorbable, and/or a biodegradable biopolymer that may provide immediate release, or sustained release of the sulindac. Examples of suitable sustained release biopolymers include but are not limited to poly (alpha-hydroxy acids), poly (lactide-co-glycolide) (PLGA), polylactide (PLA), polyglycolide (PGA), polyethylene glycol (PEG) conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG may be used as a plasticizer for PLGA, but other polymers/excipients may be used to achieve the same effect. mPEG imparts malleability to the resulting formulations. Exemplary excipients include, but are not limited, to mPEG, D-Sorbital, maltodextran, cyclodextrin, PEG, $MgCO_3$, paraffin oil, barium sulfate, paraffin oil, glycerol monooleate, tributyl-ortho-acetylcitrate (CAS: 77-90-7) (TBO-ac) or combinations thereof. The excipients, when present may for example be present in an amount of from about 0.05 wt. % to about 20 wt. %.

In various embodiments, the drug depot comprises poly (lactide-co-glycolide) (PLGA), polylactide (PLA), polyglycolide (PGA), D-lactide, D,L-lactide, L-lactide, D,L-lactide-ε-caprolactone, D,L-lactide-glycolide-ε-caprolactone, glycolide-caprolactone or a combination thereof.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methylparaben, polyvinyl alcohol and phenylethyl alcohol; solubility adjusting agents; stabilizers; and/or cohesion modifiers. If the depot is to be placed in the spinal area, in various embodiments, the depot may comprise sterile preservative free material.

The depot can be different sizes, shapes and configurations. There are several factors that can be taken into consideration in determining the size, shape and configuration of the drug depot. For example, both the size and shape may allow for ease in positioning the drug depot at the target tissue site that is selected as the implantation or injection site. In addition, the shape and size of the system should be selected so as to minimize or prevent the drug depot from moving after implantation or injection. In various embodiments, the drug depot can be shaped like a sphere, a cylinder such as a rod or fiber, a flat surface such as a disc, film or sheet or the like. Flexibility may be a consideration so as to facilitate placement of the drug depot. In various embodiments, the drug depot can be different sizes, for example, the drug depot may be a length of from about 0.5 mm to 5 mm and have a diameter of from about 0.01 to about 2 mm. In various embodiments, the drug depot may have a layer thickness of from about 0.005 to 1.0 mm, such as, for example, from 0.05 to 0.75 mm.

In various embodiments, when the drug depot comprises a pellet, it may be placed at an incision site before the site is closed. The pellet may for example be made of thermoplastic materials. Additionally, specific materials that may be advantageous for use as the pellet include but are not limited to the compounds identified above as sustained release biopolymers. The pellet may be formed by mixing the sulindac with the polymer and extruding it.

Radiographic markers can be included on the drug depot to permit the user to position the depot accurately into the target site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. Examples of such radiographic markers include, but are not limited to, barium, calcium phosphate, and/or metal beads or particles. In various embodiments, the radiographic marker could be a spherical shape or a ring around the depot.

FIG. 1 illustrates a number of common locations within a patient that may be sites at which pain and/or inflammation might occur. It will be recognized that the locations illustrated in FIG. 1 are merely exemplary of the many different locations that pain and/or inflammation might occur. For example, pain and/or inflammation may occur at a patient's knees 21, hips 22, fingers 23, thumbs 24, neck 25, and spine 26. Thus, the patient may be subjected to pain and/or inflammation and in need of pain management medication that is targeted to these sites.

Gel

In various embodiments, the gel has a pre-dosed viscosity in the range of about 1 to about 500 centipoise (cps), 1 to about 200 cps, or 1 to about 100 cps. After the gel is administered to the target site, the viscosity of the gel will increase and the gel will have a modulus of elasticity (Young's modulus) in the range of about $1 \times 10^4$ to about $6 \times 10^5$ dynes/cm$^2$, or about $2 \times 10^4$ to about $5 \times 10^5$ dynes/cm$^2$, or about $5 \times 10^4$ to about $5 \times 10^5$ dynes/cm$^2$.

In one embodiment, a depot comprises an adherent gel comprising sulindac that is evenly distributed throughout the gel. The gel may be of any suitable type, as previously indicated, and should be sufficiently viscous so as to prevent the gel from migrating from the targeted delivery site once deployed; the gel should, in effect, "stick" or adhere to the targeted tissue site. The gel may, for example, solidify upon contact with the targeted tissue or after deployment from a targeted delivery system. The targeted delivery system may be, for example, a syringe, a catheter, needle or cannula or any other suitable device. The targeted delivery system may inject the gel into or on the targeted tissue site. The therapeutic agent may be mixed into the gel prior to the gel being deployed at the targeted tissue site. In various embodiments, the gel may be part of a two-component delivery system and when the two components are mixed, a chemical process is activated to form the gel and cause it to stick or to adhere to the target tissue.

In various embodiments, a gel is provided that hardens or stiffens after delivery. Typically, hardening gel formulations may have a pre-dosed modulus of elasticity in the range of about $1 \times 10^4$ to about $3 \times 10^5$ dynes/cm$^2$, or $2 \times 10^4$ to about $2 \times 10^5$ dynes/cm$^2$, or $5 \times 10^4$ to about $1 \times 10^5$ dynes/cm$^2$. The post-dosed hardening gels (after delivery) may have a rubbery consistency and have a modulus of elasticity in the range of about $1 \times 10^4$ to about $2 \times 10^6$ dynes/cm$^2$, or about $1 \times 10^5$ to about $7 \times 10^5$ dynes/cm$^2$, or about $2 \times 10^5$ to about $5 \times 10^5$ dynes/cm$^2$.

In various embodiments, for those gel formulations that contain a polymer, the polymer concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the tissue (e.g., recesses and/or projections in bone).

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances.

In various embodiments, the molecular weight of the gel can be varied by many methods known in the art. The choice of method to vary molecular weight is typically determined by the composition of the gel (e.g., polymer, versus non-polymer). For example in various embodiments, when the gel comprises one or more polymers, the degree of polymerization can be controlled by varying the amount of polymer initiators (e.g. benzoyl peroxide), organic solvents or activator (e.g. DMPT), crosslinking agents, polymerization agent, and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel that includes a high molecular weight polymer tends to coagulate or solidify more quickly than a polymeric composition that includes a low-molecular weight polymer. Polymeric gel formulations that include high molecular weight polymers, also tend to have a higher solution viscosity than a polymeric gel that includes a low-molecular weight polymer.

When the gel is designed to be a flowable gel, it can vary from low viscosity, similar to that of water, to high viscosity, similar to that of a paste, depending on the molecular weight and concentration of the polymer used in the gel. The viscosity of the gel can be varied such that the polymeric composition can be applied to a patient's tissues by any convenient technique, for example, by spraying, brushing, dripping, injecting, or painting. Different viscosities of the gel will depend on the technique used to apply the composition.

In various embodiments, the gel has an inherent viscosity (abbreviated as "I.V." and units are in deciliters/gram), which is a measure of the gel's molecular weight and degradation time (e.g., a gel with a high inherent viscosity has a higher molecular weight and longer degradation time). Typically, a gel with a high molecular weight provides a stronger matrix and the matrix takes more time to degrade. In contrast, a gel with a low molecular weight degrades more quickly and provides a softer matrix. In various embodiments, the gel has a molecular weight, as shown by the inherent viscosity, from about 0.10 dL/g to about 1.2 dL/g or from about 0.10 dL/g to about 0.40 dL/g.

In various embodiments, the gel can have a viscosity of about 300 to about 5,000 centipoise (cp). In other embodiments, the gel can have a viscosity of from about 5 to about 300 cps, from about 10 cps to about 50 cps, from about 15 cps to about 75 cps at room temperature. The gel may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethylmethacrylate), poly-(methoxyethylmethacrylate), poly(methoxyethoxyethyl methacrylate), polymethylmethacrylate (PMMA), methylmethacrylate (MMA), gelatin, polyvinyl alcohols, propylene glycol, mPEG, PEG 1000, PEG 1450, PEG 3350, PEG 4500, PEG 8000 or combinations thereof.

A gel with a higher viscosity may be desirable for certain applications, for example, a gel having a putty-like consistency may be more preferable for bone regeneration applications. In various embodiments, when a polymer is employed in the gel, the polymeric composition includes about 10 wt % to about 90 wt % or about 30 wt % to about 60 wt % of the polymer.

In various embodiments, the gel is a hydrogel made of high molecular weight biocompatible elastomeric polymers of synthetic or natural origin. A desirable property for the hydrogel to have is the ability to respond rapidly to mechanical stresses, particularly shears and loads, in the human body.

Hydrogels obtained from natural sources are particularly appealing because they are more likely to be biodegradable and biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly (acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof.

In various embodiments, rather than directly admixing the therapeutic agent into the gel, microspheres may be dispersed within the gel, the microspheres being loaded with sulindac. In one embodiment, the microspheres provide for a sustained release of the sulindac. In yet another embodiment, the gel, which is biodegradable, prevents the microspheres from releasing the sulindac; the microspheres thus do not release the sulindac until they have been released from the gel. For example, a gel may be deployed around a target tissue site (e.g., a nerve root). Dispersed within the gel are a plurality of microspheres that encapsulate the desired therapeutic agent. Certain of these microspheres degrade once released from the gel, thus releasing the sulindac.

Microspheres, much like a fluid, may disperse relatively quickly, depending upon the surrounding tissue type, and hence disperse the sulindac. In some embodiments, the diameter of the microspheres range from about 10 to about 200 microns in diameters. In some embodiments, they range from about 20 to about 120 microns in diameter. In some situations, this may be desirable; in others, it may be more desirable to keep the sulindac tightly constrained to a well-defined target site. The present invention also contemplates the use of adherent gels to so constrain dispersal of the therapeutic agent. These gels may be deployed, for example, in a disc space, in a spinal canal, or in surrounding tissue.

Drug Delivery

It will be appreciated by those with skill in the art that the depot can be administered to the target site using a "cannula" or "needle" that can be a part of a drug delivery device e.g., a syringe, a gun drug delivery device, or any medical device suitable for the application of a drug to a targeted organ or anatomic region. The cannula or needle of the drug depot device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. In various embodiments, the cannula or needle may be inserted using a transforaminal approach in the spinal foramen space, for example, along an inflamed nerve root and the drug depot implanted at this site for treating the condition. Typically, the transforaminal approach involves approaching the intervertebral space through the intervertebral foramina.

Some examples of lengths of the cannula or needle may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 to about 1.655 mm. The gauge of the cannula or needle may be the widest or smallest diameter or a diameter in between for insertion into a human or animal body. The widest diameter is typically about 14 gauge, while the smallest diameter is about 25 gauge. In various embodiments the gauge of the needle or cannula is about 18 to about 22 gauge.

In various embodiments, like the drug depot and/or gel, the cannula or needle includes dose radiographic markers that indicate location at or near the site beneath the skin, so that the user may accurately position the depot at or near the site using any of the numerous diagnostic imaging procedures. Such diagnostic imaging procedures include, for example, X-ray imaging or fluoroscopy. Examples of such radiographic markers include, but are not limited to, barium, calcium, and/or metal beads or particles.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

The drug depot, and/or medical device to administer the drug may be sterilizable. In various embodiments, one or more components of the drug depot, and/or medical device to administer the drug are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot is included in a gel.

Other methods may also be used to sterilize the depot and/or one or more components of the device, including, but not limited to, gas sterilization, such as, for example, with ethylene oxide or steam sterilization.

Kits

In various embodiments, a kit is provided that may include additional parts along with the drug depot and/or medical device combined together to be used to implant the drug depot (e.g., pellets). The kit may include the drug depot device in a first compartment. The second compartment may include a canister holding the drug depot and any other instruments needed for the localized drug delivery. A third compartment may include gloves, drapes, wound dressings and other procedural supplies for maintaining sterility of the implanting process, as well as an instruction booklet. A fourth compartment may include additional cannulas and/or needles. A fifth compartment may include an agent for radiographic imaging. Each tool may be separately packaged in a plastic pouch that is radiation sterilized. A cover of the kit may include illustrations of the implanting procedure and a clear plastic cover may be placed over the compartments to maintain sterility.

Administration

In various embodiments, the drug depot containing the sulindac may be parenterally administered. In addition to including administration that is intravenous, intramuscular, through continuous or intermittent infusion, intraperitoneal, intrasternal, subcutaneous, intra-operatively, intrathecally, intradiscally, peridiscally, epidurally, perispinally, intra-articularly or a combination thereof, parenteral administration also includes an infusion pump that administers a pharmaceutical composition through a catheter near the target site, an implantable mini-pump that can be inserted at or near the target site, and/or an implantable controlled release device or sustained release delivery system that can release a certain amount of the composition per hour or in intermittent bolus doses.

One example of a suitable pump for use is the SynchroMed® (Medtronic, Minneapolis, Minn.) pump. The pump has three sealed chambers. One contains an electronic module and battery. The second contains a peristaltic pump and drug reservoir. The third contains an inert gas, which provides the pressure needed to force the pharmaceutical composition into the peristaltic pump. To fill the pump, the pharmaceutical composition is injected through the reservoir fill port to the expandable reservoir. The inert gas creates pressure on the reservoir, and the pressure forces the pharmaceutical composition through a filter and into the pump chamber. The pharmaceutical composition is then pumped out of the device from the pump chamber and into the catheter, which will direct it for deposit at the target site. The rate of delivery of pharmaceutical composition is controlled by a microprocessor. This allows the pump to be used to deliver similar or different amounts of pharmaceutical composition continuously, at specific times, or at set intervals.

Potential drug delivery devices suitable for adaptation for the methods described herein include but are not limited to those described, for example, in U.S. Pat. No. 6,551,290 (assigned to Medtronic, the entire disclosure of which is herein incorporated by reference), which describes a medical catheter for target specific drug delivery; U.S. Pat. No. 6,571,125 (assigned to Medtronic, the entire disclosure of which is herein incorporated by reference), which describes an implantable medical device for controllably releasing a biologically active agent; U.S. Pat. No. 6,594,880 (assigned to Medtronic, the entire disclosure of which is herein incorporated by reference), which describes an interparenchymal infusion catheter system for delivering therapeutic agents to selected sites in an organism; and U.S. Pat. No. 5,752,390 (assigned to Medtronic, the entire disclosure of which is herein incorporated by reference), which describes an implantable catheter for infusing equal volumes of agents to spaced sites. In various embodiments, pumps may be adapted with a pre-programmable implantable apparatus with a feedback regulated delivery, a micro-reservoir osmotic release system for controlled release of chemicals, small, lightweight devices for delivering liquid medication, implantable micro-miniature infusion devices, implantable ceramic valve pump assemblies, or implantable infusion pumps with a collapsible fluid chamber. Alzet® osmotic pumps (Durect Corporation, Cupertino, Calif.) are also available in a variety of sizes, pumping rates, and durations suitable for use in the described methods.

In various embodiments, a method for delivering a therapeutic agent into a surgery site of a patient is provided, the method comprising inserting a cannula at or near a target tissue site and implanting the drug depot at the target site beneath the skin of the patient and spraying, brushing, dripping, injecting, or painting the gel in the target site to hold or have the drug depot adhere to the target site. In this way unwanted migration of the drug depot away from the target site is reduced or eliminated.

In various embodiments, to administer the gel having the drug depot dispersed therein to the desired site, first the cannula or needle can be inserted through the skin and soft tissue down to the target tissue site and the gel administered (e.g., brushed, dripped, injected, or painted, etc.) at or near the target site. In those embodiments where the drug depot is separate from the gel, first the cannula or needle can be inserted through the skin and soft tissue down to the site of injection and one or more base layer(s) of gel can be administered to the target site. Following administration of the one or more base layer(s), the drug depot can be implanted on or in the base layer(s) so that the gel can hold the depot in place or reduce migration. If required a subsequent layer or layers of gel can be applied on the drug depot to surround the depot and further hold it in place. Alternatively, the drug depot may be implanted first and then the gel placed (e.g., brushed, dripped, injected, or painted, etc.) around the drug depot to hold it in place. By using the gel, accurate and precise implantation of a drug depot can be accomplished with minimal physical and psychological trauma to the patient. The gel also avoids the need to suture the drug depot to the target site reducing physical and psychological trauma to the patient.

In various embodiments, when the target site comprises a spinal region, a portion of fluid (e.g., spinal fluid, etc.) can be withdrawn from the target site through the cannula or needle first and then the depot administered (e.g., placed, dripped, injected, or implanted, etc.). The target site will re-hydrate (e.g., replenishment of fluid) and this aqueous environment will cause the drug to be released from the depot.

Figure 2:
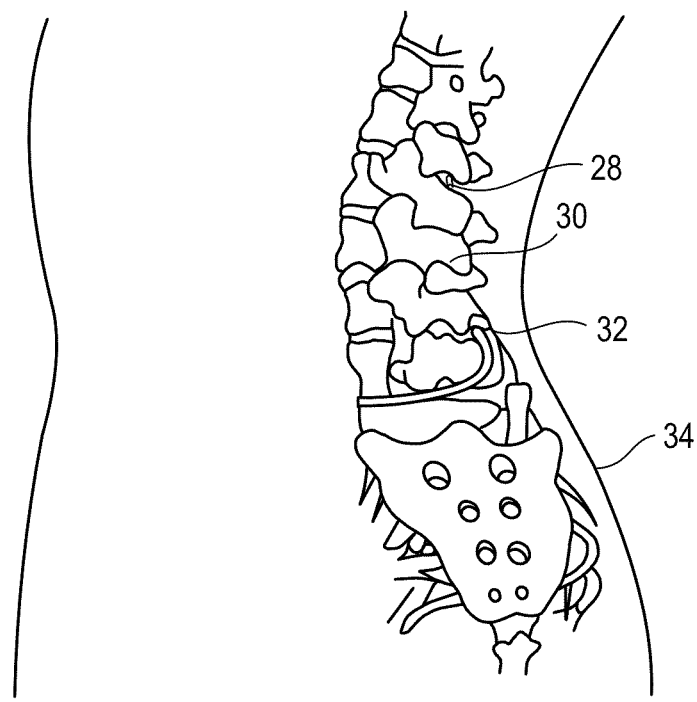
FIG. 2 illustrates a schematic dorsal view of the spine and sites where the drug depot containing sulindac can locally be administered thereto.

One exemplary embodiment where the depot is suitable for use in treating pain (e.g., neuropathic pain management) and/or to treat conditions (e.g., sciatica) is illustrated in FIG. 2. Schematically shown in FIG. 2 is a dorsal view of the spine and sites where the drug depot may be inserted using a cannula or needle beneath the skin 34 to a spinal site 32 (e.g., spinal disc space, spinal canal, soft tissue surrounding the spine, nerve root, etc.) and one or more drug depots 28 and 32 are delivered to various sites along the spine. In this way, when several drug depots are to be implanted, they are implanted in a manner that optimizes location, accurate spacing, and drug distribution.

Although the spinal site is shown, as described above, the drug depot can be delivered to any site beneath the skin, including, but not limited to, at least one muscle, ligament, tendon, cartilage, spinal disc, spinal foraminal space, near the spinal nerve root, or spinal canal.

The sulindac-based formulation of the present invention may be used as medicaments in the form of pharmaceutical preparations. The preparations may be formed in an administration with a suitable pharmaceutical carrier that may be solid or liquid and organic or inorganic, and placed in the appropriate form for parenteral or other administration as desired. As persons of ordinary skill are aware, known carriers include but are not limited to water, gelatine, lactose, starches, stearic acid, magnesium stearate, sicaryl alcohol, talc, vegetable oils, benzyl alcohols, gums, waxes, propylene glycol, polyalkylene glycols and other known carriers for medicaments.

Another embodiment of the present invention is directed to a method for treating a mammal suffering from pain and/or inflammation, said method comprising administering a therapeutically effective amount of sulindac at a target site beneath the skin. The sulindac (or pharmaceutically acceptable salt) may for example be administered locally to the target tissue site as a drug depot.

In some embodiments, the sulindac is encapsulated in a plurality of depots comprising microparticles, microspheres, microcapsules, and/or microfibers.

In some embodiments there is a method for making an implantable drug depot. The method may comprise combining a biocompatible polymer and a therapeutically effective amount of sulindac or a pharmaceutically acceptable salt thereof and forming the implantable drug depot from the combination.

In some embodiments, the sulindac is suitable for parenteral administration. The term "parenteral" as used herein refers to modes of administration, which bypass the gastrointestinal tract, and include for example, intravenous, intramuscular, continuous or intermittent infusion, intraperitoneal, intrasternal, subcutaneous, intra-operatively, intrathecally, intradiscally, peridiscally, epidurally, perispinally, intraarticular injection or combinations thereof. In some embodiments, the injection is intrathecal, which refers to an injection into the spinal canal (intrathecal space surrounding the spinal cord). An injection may also be into a muscle or other tissue. In other embodiments, the sulindac is administered by placement into an open patient cavity during surgery itself.

In various embodiments, the drug depot comprising the sulindac can be made by combining a biocompatible polymer and a therapeutically effective amount of sulindac or pharmaceutically acceptable salt thereof and forming the implantable drug depot from the combination.

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: sulindac and other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: sulindac, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, sulindac may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with therapeutic agent under conditions of lower temperature and mechanical shear, and the resulting mixture is shaped into the sulindac containing drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear (e.g., sulindac), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of sulindac because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion process may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., pellet, strip, etc.) is cooled. Examples of cooling processes include air cooling and/or immersion in a cooling bath. In some embodiments, a water bath is used to cool the extruded depot. However, where a water-soluble therapeutic agent such as sulindac is used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired.

In various embodiments, the drug depot can be prepared by mixing or spraying the drug with the polymer and then molding the depot to the desired shape. In various embodiments, sulindac is used and mixed or sprayed with the PLGA or PEG550 polymer, and the resulting depot may be formed by extrusion and dried.

In various embodiments, there is a pharmaceutical formulation comprising: sulindac, wherein the sulindac comprises from about 20 wt. % to about 40 wt. % of the formulation, and at least one biodegradable polymer. In some embodiments, the sulindac comprises from about 5 wt. % to about 15 wt. % or about 7.5 wt. % to about 12.5 wt. % of the formulation In some embodiments, the at least one biodegradable polymer comprises poly(lactic-co-glycolic acid) (PLA) or poly(orthoester) (POE) or a combination thereof. The poly(lactic-co-glycolic acid) may comprise a mixture of polyglycolide (PGA) and polylactide and in some embodiments, in the mixture, there is more polylactide than polyglycolide. In various other embodiments in which the polymer or one of the polymers is poly(lactic-co-glycolic acid), there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the poly(lactic-co-glycolic acid) is polyglycolide.

In some embodiments, the biodegradable polymer comprises at least 50 wt. % of the formulation, at least 60 wt. % of the formulation, at least 70 wt. % of the formulation, at least 80 wt. % of the formulation, at least 85 wt. % of the formulation, at least 90 wt. % of the formulation, at least 95 wt. % of the formulation or at least 99 wt. % of the formulation. In some embodiments, the at least one biodegradable polymer and the sulindac are the only components of the pharmaceutical formulation.

In some embodiments, at least 75% of the particles have a size from about 10 micrometer to about 200 micrometers. In some embodiments, at least 85% of the particles have a size from about 10 micrometer to about 200 micrometers. In some embodiments, at least 95% of the particles have a size from about 10 micrometer to about 200 micrometers. In some embodiments, all of the particles have a size from about 10 micrometer to about 2000 micrometers.

In some embodiments, at least 75% of the particles have a size from about 20 micrometer to about 180 micrometers. In some embodiments, at least 85% of the particles have a size from about 20 micrometers to about 180 micrometers. In some embodiments, at least 95% of the particles have a size from about 20 micrometer to about 180 micrometers. In some embodiments, all of the particles have a size from about 20 micrometer to about 180 micrometers.

In some embodiments, there is a pharmaceutical formulation comprising: sulindac, wherein the sulindac comprises from about 20 wt. % to about 40 wt. % of the formulation, and at least one biodegradable polymer, wherein the at least one biodegradable polymer comprises poly(lactic-co-glycolic acid) or poly(orthoester) or a combination thereof, and said at least one biodegradable polymer comprises at least 80 wt. % of said formulation.

In some embodiments, there are methods for treating pain and/or inflammation. These methods comprise: administering a pharmaceutical composition to an organism, wherein said pharmaceutical composition comprises from about 20 wt. % to about 40 wt. % of the formulation, and at least one biodegradable polymer.

In some embodiment there is a higher loading of sulindac, e.g., at least 40 wt. %, at least 50 wt. %, at least 60 wt. %, at least 70 wt. %, at least 80 wt. %, at least 90 wt. %.

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances. In some embodiments, the polymer comprises 20 wt. % to 90 wt. % of the formulation.

In various embodiments, the molecular weight of the gel can be varied by many methods known in the art. The molecular weight of the polymer can be varied to regulate the release rate profile and/or delivery duration of the active ingredient. In general, as the molecular weight of the polymer increases, one or more of the following occurs: the burst index is lower, the release profile is flatter and/or the duration of delivery is longer. The choice of method to vary molecular weight is typically determined by the composition of the gel (e.g., polymer, versus non-polymer). For example in various embodiments, when the gel comprises one or more polymers, the degree of polymerization can be controlled by varying the amount of polymer initiators (e.g., benzoyl peroxide), organic solvents or activator (e.g., DMPT), crosslinking agents, polymerization agent, and/or reaction time. By was of a non-limiting example, the polymer make up may comprise from 50:50 PLGA to 100 PLA and the molecular weight range may be from 0.45 to 0.8 dL/g.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel that includes a high molecular weight polymer tends to coagulate or solidify more quickly than a polymeric composition, which includes a low-molecular weight polymer. Polymeric gel formulations that include high molecular weight polymers, also tend to have a higher solution viscosity than a polymeric gel, which include a low-molecular weight polymer.

As persons of ordinary skill in the art are aware, implantable elastomeric depot compositions having a blend of polymers with different end groups are used the resulting formulation will have a lower burst index and a regulated duration of delivery. For example, one may use polymers with acid (e.g., carboxylic acid) and ester end groups (e.g., lauryl, methyl or ethyl ester end groups).

Additionally, by varying the comonomer ratio of the various monomers that form a polymer (e.g., the L/G/CL or G/CL ratio for a given polymer) there will be a resulting depot composition having a regulated burst index and duration of delivery. For example, a depot composition having a polymer with a L/G ratio of 50:50 may have a short duration of delivery ranging from about two days to about one month; a depot composition having a polymer with a L/G ratio of 65:35 may have a duration of delivery of about two months; a depot composition having a polymer with a L/G ratio of 75:25 or L/CL ratio of 75:25 may have a duration of delivery of about three months to about four months; a depot composition having a polymer ratio with a L/G ratio of 85:15 may have a duration of delivery of about five months; a depot composition having a polymer with a L/CL ratio of 25:75 or PLA may have a duration of delivery greater than or equal to six months; a depot composition having a terpolymer of CL/G/L with G greater than 50% and L greater than 10% may have a duration of delivery of about one month and a depot composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery.

Thus, depot compositions having a blend of polymers having different molecular weights, end groups and comonomer ratios can be used to create a depot formulation having a lower burst index and a regulated duration of delivery.

A strategy of triangulation may be effective when administering these pharmaceutical formulations. Thus, a plurality (at least two, at least three, at least four, at least five, at least six, at least seven, etc.) drug depots comprising the pharmaceutical formulations may be placed around the target tissue site (also known as the pain generator or pain generation site) such that the target tissue site falls within a region that is either between the formulations when there are two, or within an area whose perimeter is defined by a set of plurality of formulations.

In some embodiments, the formulations are slightly rigid with varying length, widths, diameters, etc. For example, certain formulations may have a diameter of 0.50 mm and a length of 4 mm. It should be noted that particle size may be altered by techniques such as using a mortar and pestle, jet-drying or jet milling.

In some embodiments, sulindac is released at a rate of 5-15 mg/per day, or 7-12 mg/day or 8-10 mg/day for a period of at least three to twenty-five days. In some embodiments, this release rate lasts for, at least fifty days, at least ninety days, at least one hundred days, at least one-hundred and thirty-five days, at least one-hundred and fifty days, or at least one hundred and eighty days.

For some embodiments, 625-2025 milligrams of sulindac as formulated with a biopolymer are implanted into a person at or near a target tissue site. For some embodiments, 945-1620 milligrams of sulindac as formulated with a biopolymer are implanted into a person at or near a target tissue site. For some embodiments, 1080-1325 milligrams of sulindac as formulated with a biopolymer are implanted into a person at or near a target tissue site.

If sulindac is implanted at multiple sites that triangulate the target site then in some embodiments, the total amount of sulindac at each site is a fraction of the total number of milligrams. For example, one may implant a single does of 1296 milligrams at one site, or two separate doses of 648 micrograms at two sites, or three separate dose of 432 milligrams at three sites that triangulate the tissue site. It is important to limit the total dosage to an amount less than that which would be harmful to the organism. However, in some embodiments, although when there are a plurality of sites each site may contain less than the total does that might have been administered in a single application, it is important to remember that each site will independent have a release profile, and the biopolymers' concentration and substance should be adjusted accordingly to ensure that the sustain release occurs over sufficient time.

In one embodiment of the present invention, the sulindac and the dosage is from approximately 0.001 µg/day to approximately 100 mg/day. Additional dosages of sulindac can include from approximately 0.001 µg/day to approximately 200 mg/day; approximately 0.001 µg/day to approximately 100 mg/day; approximately 0.001 µg/day to approximately 1 mg/day; approximately 0.001 µg/day to approximately 500 µg/day; approximately 0.001 µg/day to approximately 100 µg/day; approximately 0.025 to approximately 75 µg/day; approximately 0.025 µg/day to approximately 65 µg/day; approximately 0.025 µg/day to approximately 60 µg/day; approximately 0.025 µg/day to approximately 55 µg/day; approximately 0.025 µg/day to approximately 50 µg/day; approximately 0.025 µg/day to approximately 45 µg/day; approximately 0.025 µg/day to approximately 40 µg/day; approximately 0.025 µg/day to approximately 35 µg/day; approximately 0.005 to approximately 30 µg/day; approximately 0.005 to approximately 25 µg/day; approximately 0.005 µg/day to approximately 20 µg/day; and approximately 0.005 µg/day to approximately 15 µg/day. In another embodiment, the dosage of sulindac is from approximately 0.01 µg/day to approximately 15 µg/day. In another embodiment, the dosage of sulindac is from approximately 0.01 µg/day to approximately 10 µg/day. In another embodiment, the dosage of sulindac is from approximately 0.01 µg/day to approximately 5 µg/day. In another embodiment, the dosage of sulindac is from approximately 0.01 µg/day to approximately 20 µg/day. In another embodiment, sulindac is administered in a drug depot that releases 9.6 µg/day.

In some embodiments, there is a drug depot comprising sulindac or sulindac and a polymer, wherein the polymer is one more of poly(lactide-co-glycolide) (PLGA), D-lactide, D,L-lactide, L-lactide, D,L-lactide-caprolactone, D,L-lactide-glycolide-caprolactone, or glycolide-caprolactone.

The potency of sulindac is the complicating factor. Sulindac is not a potent molecule, and as such, in some embodiments it is desirable to provide sufficient sulindac to permit the active ingredient to be delivered at a rate of about 9.6 mg/day for a desired time period. By way of example, exemplary formulations include 20% sulindac in 85/15 PLGA 7E+10% mPEG 550) and 20% sulindac in 100 DL 7E.

In one exemplary dosing regimen, a rat is provided with sufficient sulindac in a biodegradable polymer to provide sustain release of 0.96 µg/day for 135 days. The total amount of sulindac that is administered over this time period would be approximately 129.6 µg. In another exemplary dosing regimen, a human is provided with sufficient sulindac in a biodegradable polymer to provide sustain release of 9.6 µg/day for 135 days. The total amount of sulindac that is administered over this time period would be approximately 1296 µg. In third exemplary dosing regimen an animal is given 2 mg/kg/day of sulindac for a period of at least fifteen days.

Having now generally described the invention, the same may be more readily understood through the following reference to the following examples, which are provided by way of illustration and are not intended to limit the present invention unless specified.

EXAMPLES

Example 1

Exemplary Formulations

A number of formulations were created and are summarized in Table 1, Table 2 and Table 4 below.

TABLE 1

First set of exemplary sulindac formulations

| Polymer | Drug Load (wt %) |
|---|---|
| 100 DL 7E | 14.2 |
| 100 DL 7E | 20.4 |
| 8515 DLG 7E | 14.4 |
| 8515 DLG 7E | 19.2 |
| 100 DL 5E | 14.8 |
| 100 DL 5E | 19 |
| 100 DL 7E | 30.7 |
| 100 DL 7E | 40.7 |
| 100 DL 7E | 19.2 |
| 100 DL 7E | 27.1 |
| 8515 DLG 7E | 28.8 |

The codes within table 1 for the polymer are explained as follows. The first number or numbers refers to monomer mole percentage ratio of DL-lactide (e.g., polylactide) to glycolide (e.g., poly-glycolide). The letter code that follows the first number refers to the polymer(s) and is the polymer identifier. The second number, which follow the letter code for the polymer, is the target IV designator and is 10 times the midpoint of a range in dl/g. The meanings of certain IV designators are reflected in Table 3.

TABLE 3

| IV Target Designator | IV Range |
|---|---|
| 1 | 0.05-0.15 |
| 1.5 | 0.10-0.20 |
| 2 | 0.15-0.25 |
| 2.5 | 0.20-0.30 |
| 3 | 0.25-0.35 |
| 3.5 | 0.30-0.40 |
| 4 | 0.35-0.45 |
| 4.5 | 0.40-0.50 |
| 5 | 0.45-0.55 |
| 6 | 0.50-0.70 |
| 7 | 0.60-0.80 |
| 8 | 0.70-0.90 |
| 9 | 0.80-1.0 |

The final letter within the code of the polymer is the end group designator. For examples "E" refers to an ester end group, while "A" refers to an acid end group.

By way of example, 100 ☐L 7E is a polymer that has an inherent viscosity of 0.60-0.80 dL/g. It contains 100% poly (DL-lactide) that has ester end groups. It is available from Lakeshore Biomaterials, Birmingham, Ala.

Table 2 in FIGS. 5 and 6 shows a set of exemplary sulindac formulations.

Sulindac drug loads ranged from 0.4 wt % to 30 wt. %. The polymers included PLGA 85/15, 75/25, or 50/50, DL, POE, or DL-PLA. The excipients include mPEG, PEG, barium sulfate with mPEG, magnesium carbonate, paraffin oil, PEG, glycerol monooleate, TBO-AC, or no excipients. Excipients may be added in weight percentages from 0.001 wt % or 0.01 wt. % to 50 wt. %, 5 to 25 wt %, or 5 to 12 wt %.

In vitro elution profiles (shown in FIGS. 7-16) were obtained from about 3 to 150 days, which may be useful for treating pain and/or inflammation in conditions such as, for example, sciatica.

Figure 17:
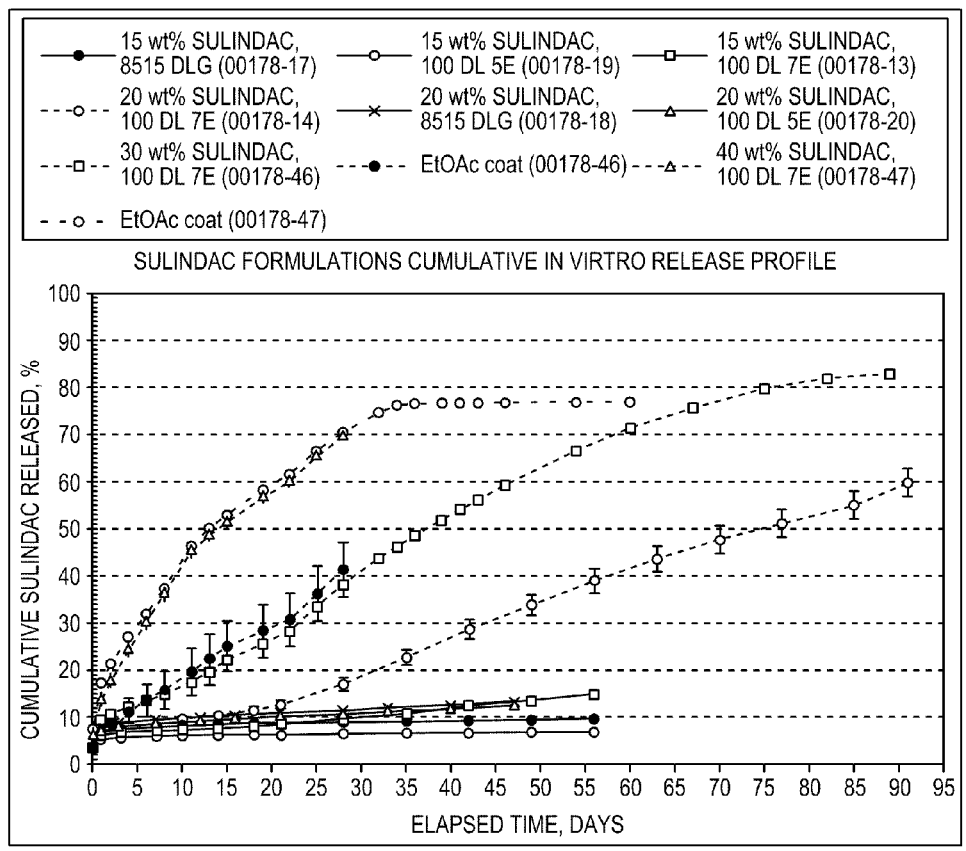
Figure 18:
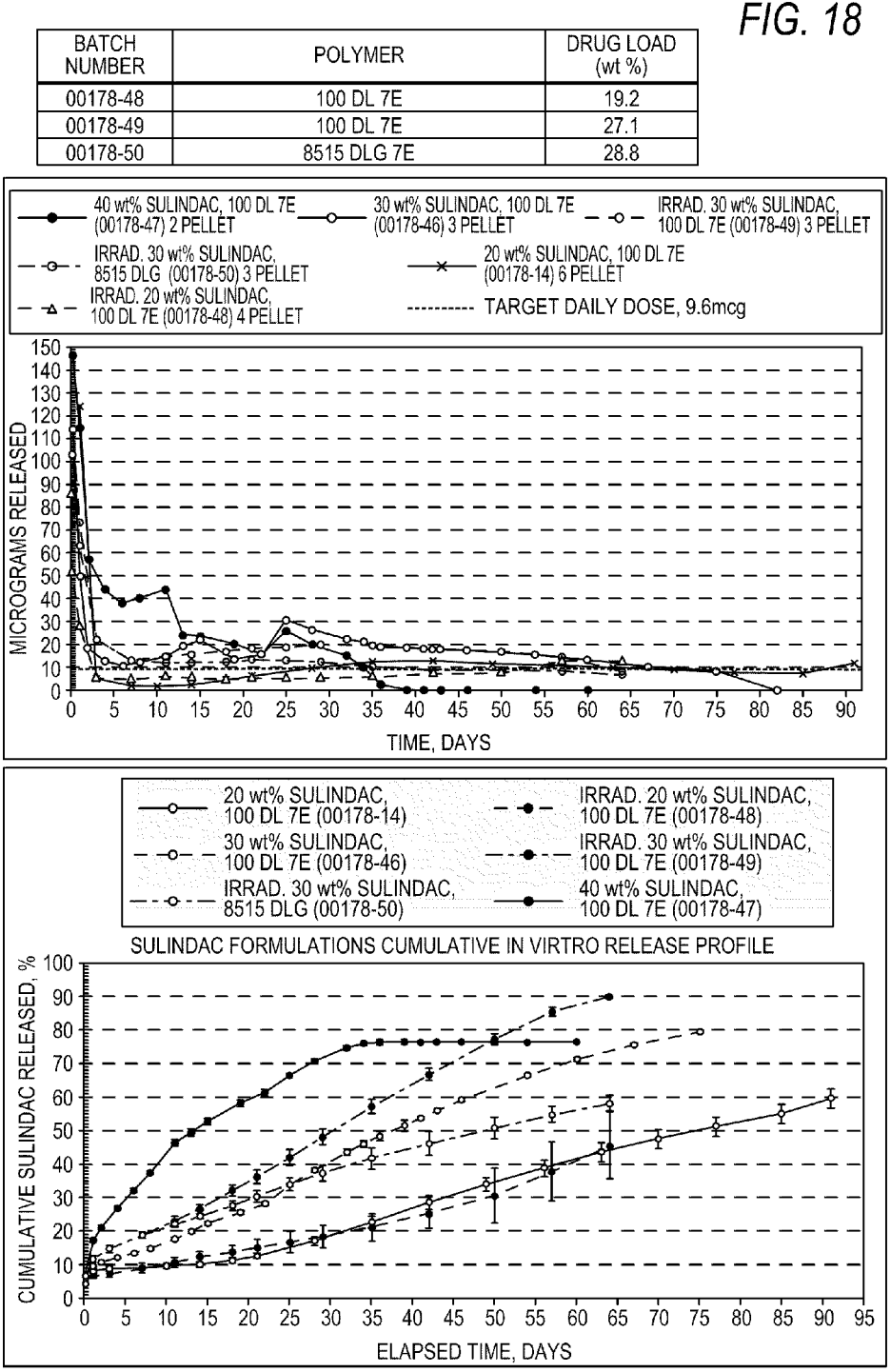

A separate batch of sulindac formulations (shown in FIGS. 17-18) and their respective In Vitro elution profiles are shown ranging from about 40 to 90 days, which may be useful for treating pain and/or inflammation in conditions such as, for example, sciatica.

Example 2

Testing in Rat

The inventors evaluated the efficacy of a 5 Month Sulindac/Polymer Drug Depot in the Rat Chronic Constriction Injury Model. The animal model was the Bennett Model (Wistar rat). The purpose: To determine whether a 5 month polymer sulindac-eluting depot can improve pain associated behavioral responses in a rat model of neuropathic pain.

Experimental Design: Four loose chromic gut ligatures, 1 mm apart, were tied around the common sciatic nerve at mid-thigh. Each animal received treatment of test or control article-according to the dosing described in Table 4.

TABLE 4

| Group Number | Treatment |
|---|---|
| 1 | Sulindac 0.4 mg/kg |
| 2 | 85/15 PLGA Control |
| 3 | 85/15 PLGA-20% |
| 4 | 85/15 PLGA-27% |
| 5 | DL-PLA-25% |
| 6 | 100-DL-7E-30% |
| 7 | 100-DL-7E-20% |
| 8 | 85/15 PLGA-30% |

Figure 3:
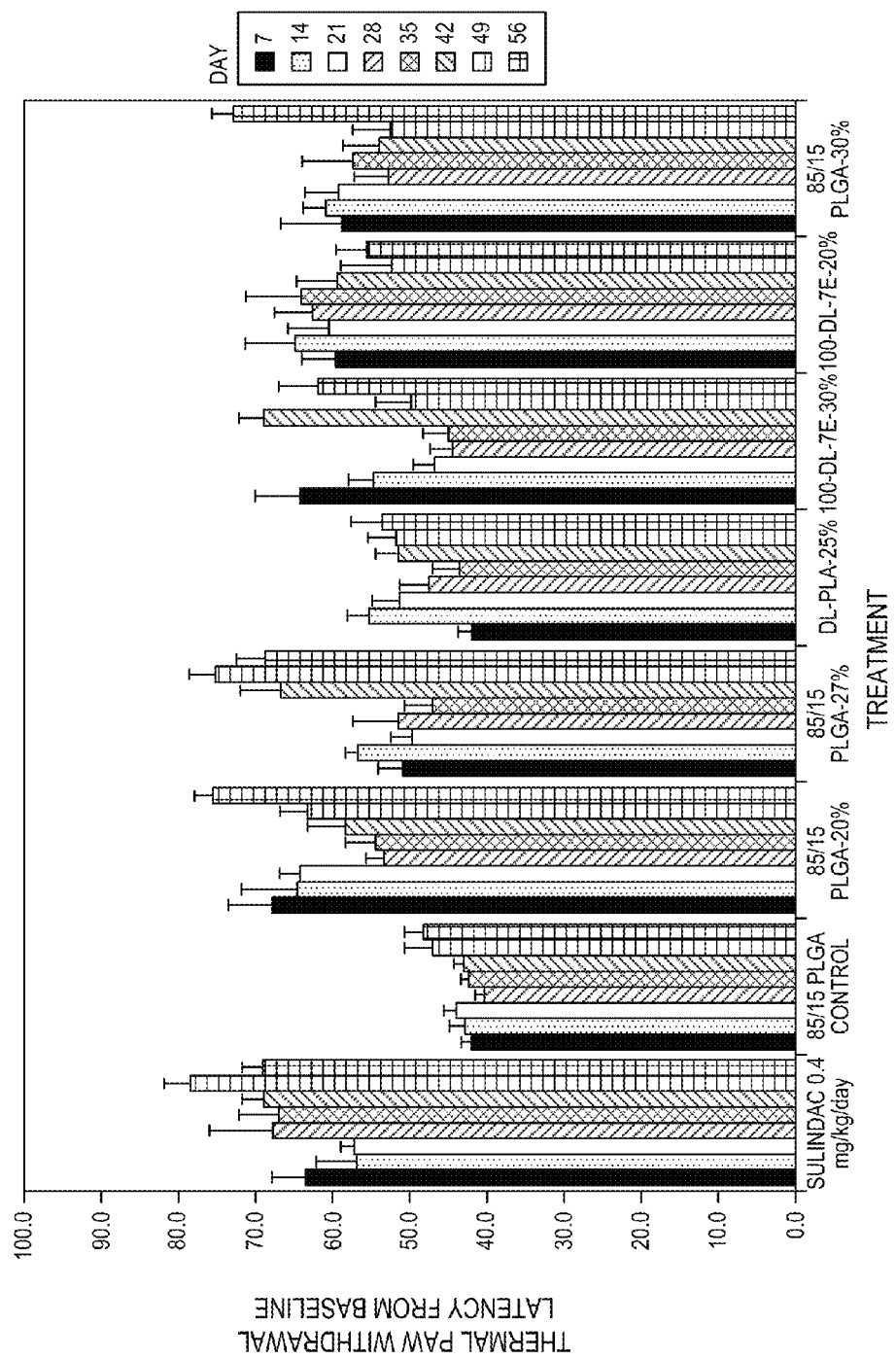
FIG. 3 is a graphic representation of the thermal paw withdrawal latency as a percentage from baseline for the following administrations: sulindac 0.4 mg/kg/day IP, 85/15 PLGA control, 85/15 PLGA-20%, 85/15 PLGA-27%, DL-PLA-25%, 100-DL-7E-30%, 100-DL-7E-20% and 85/15 PLGA-30% at 7, 14, 21, 28, 35, 42, 49, and 57 days.
Figure 4:
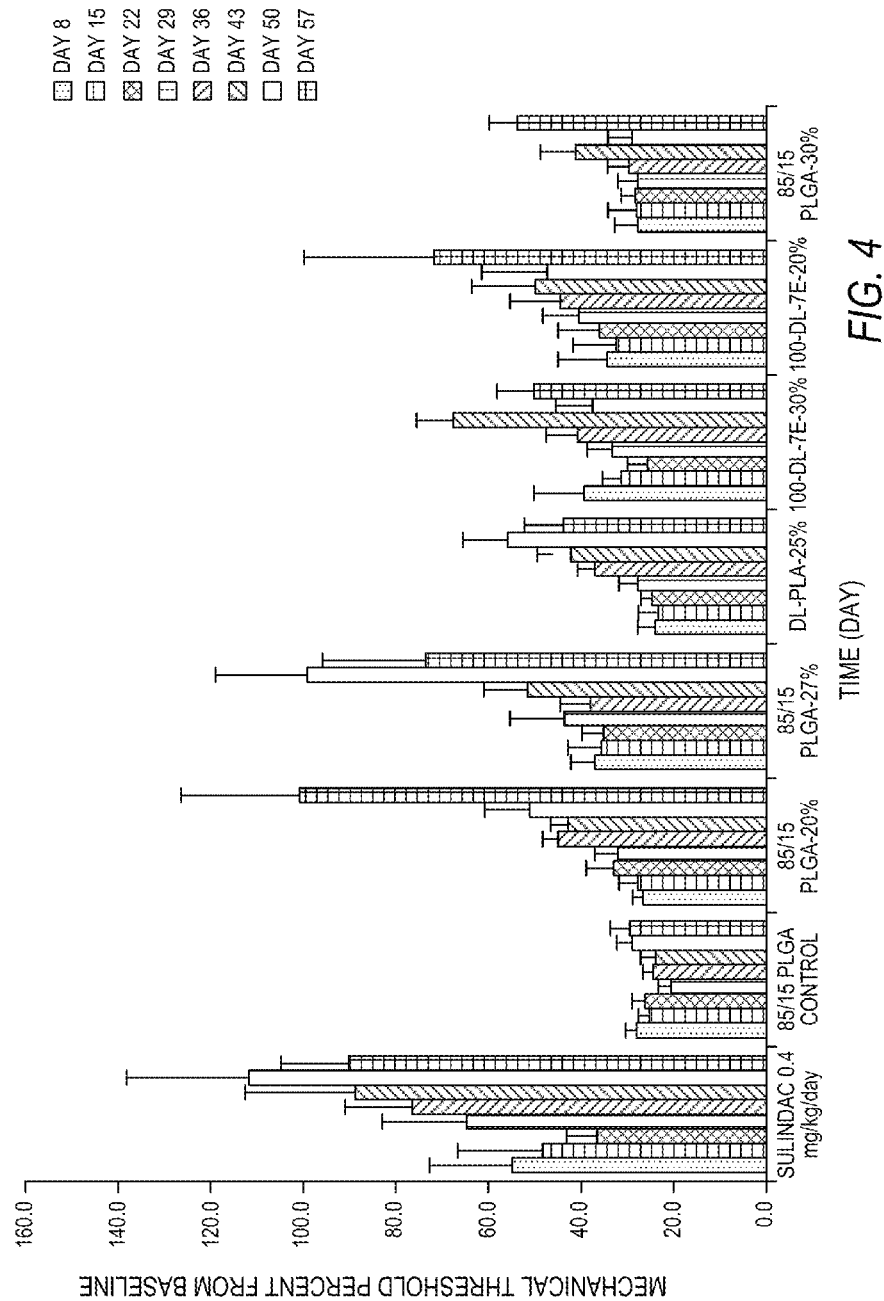
FIG. 4 is a graphic representation of the mechanical threshold as a percentage from baseline for sulindac 0.4 mg/kg/day IP, 85/15 PLGA control, 85/15 PLGA-20%, 85/15 PLGA-27%, DL-PLA-25%, 100-DL-7E-30%, 100-DL-7E-20% and 85/15 PLGA-30% at 8, 15, 22, 29, 36, 43, 50, and 57 days.
Figure 8:
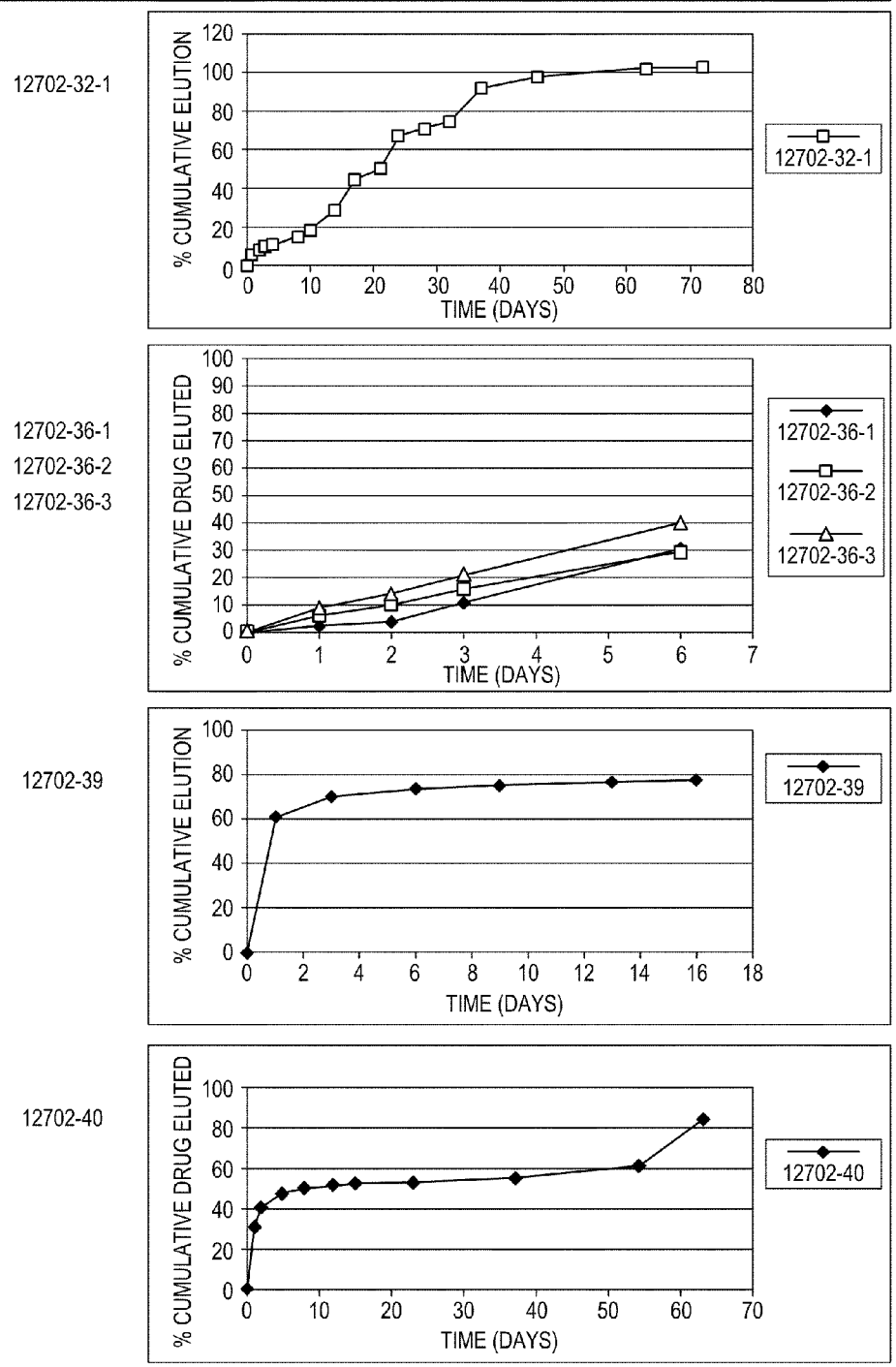
Figure 9:
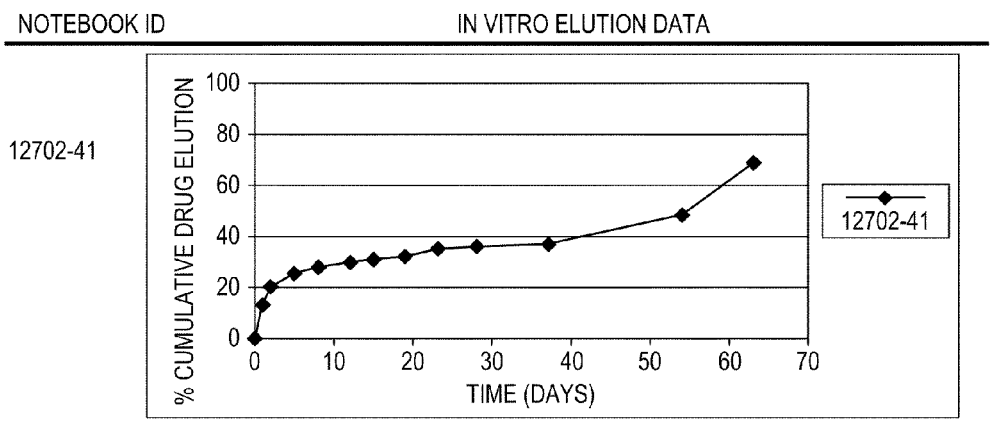
Figure 10:
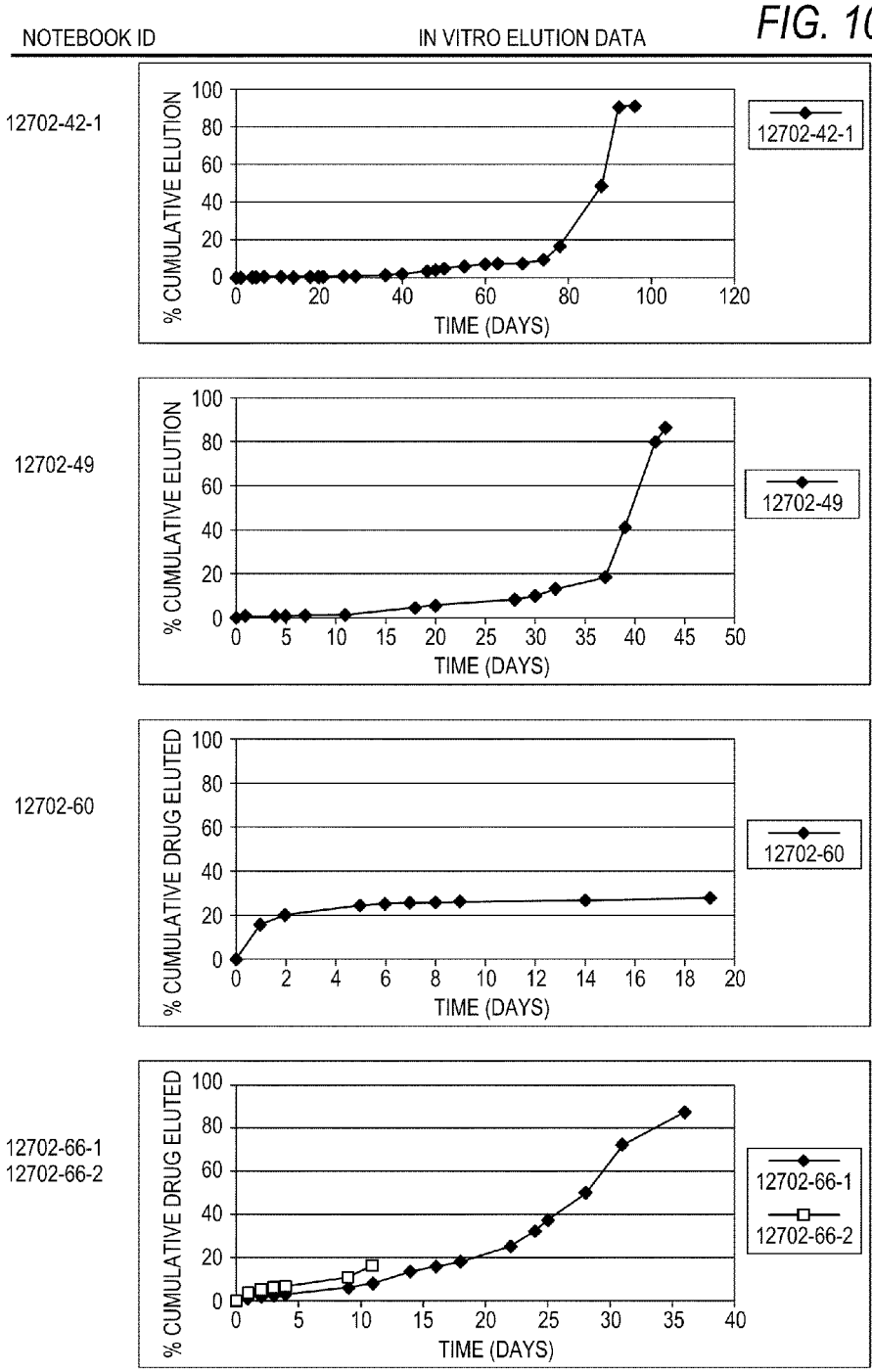
Figure 11:
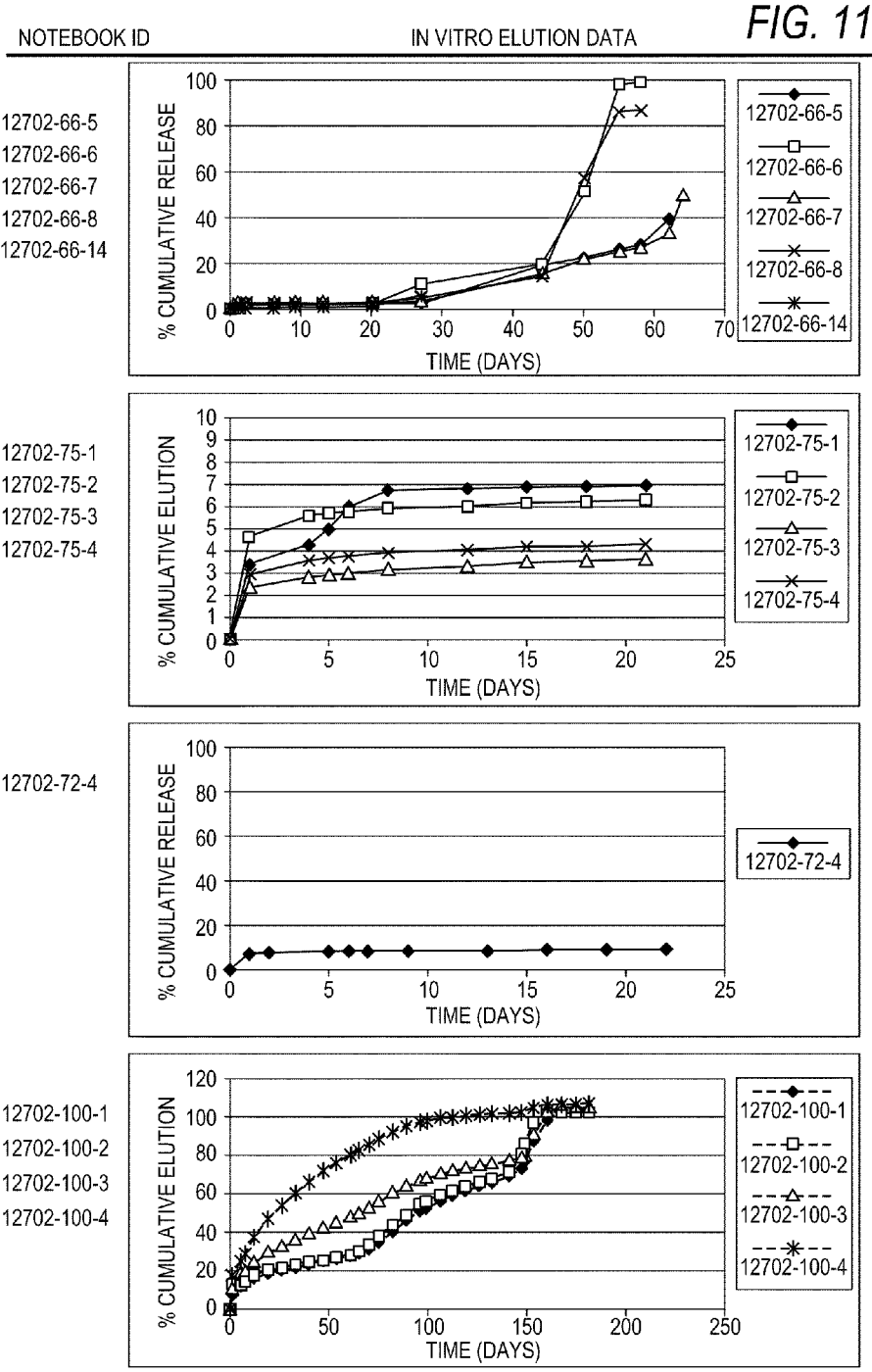
Figure 12:
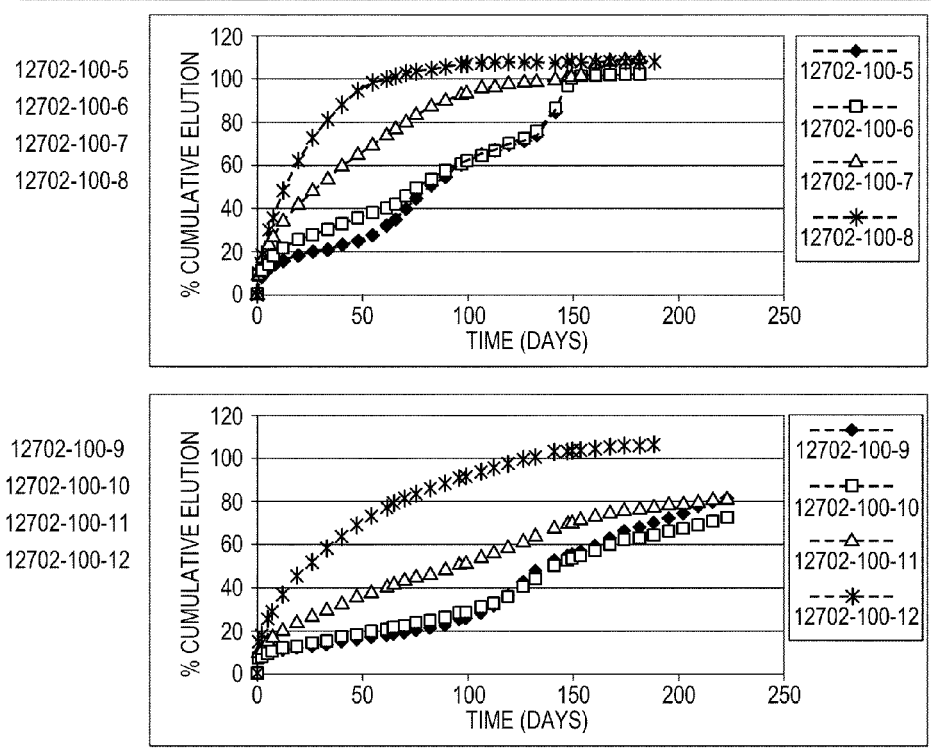
Figure 13:
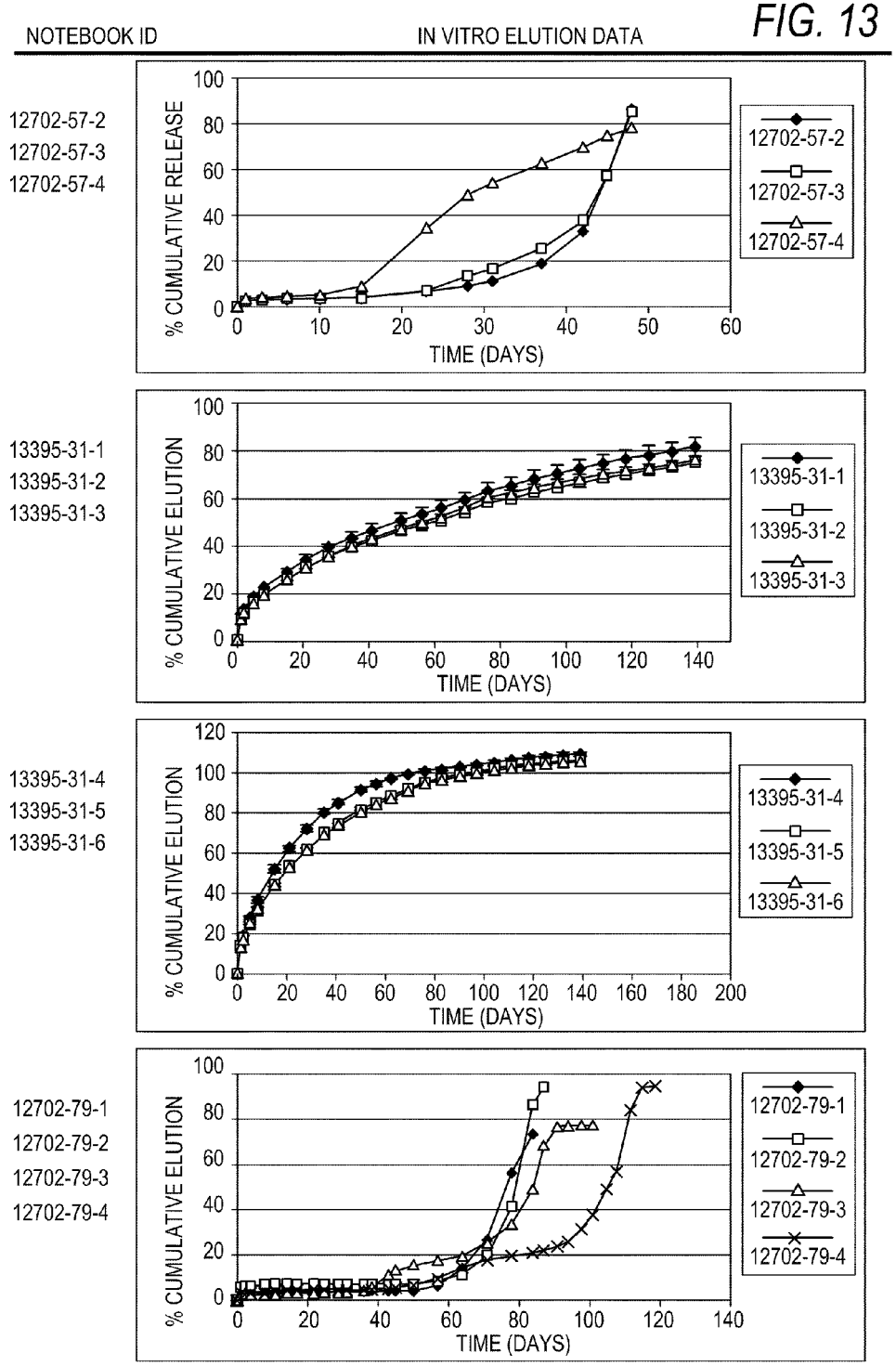
Figure 14:
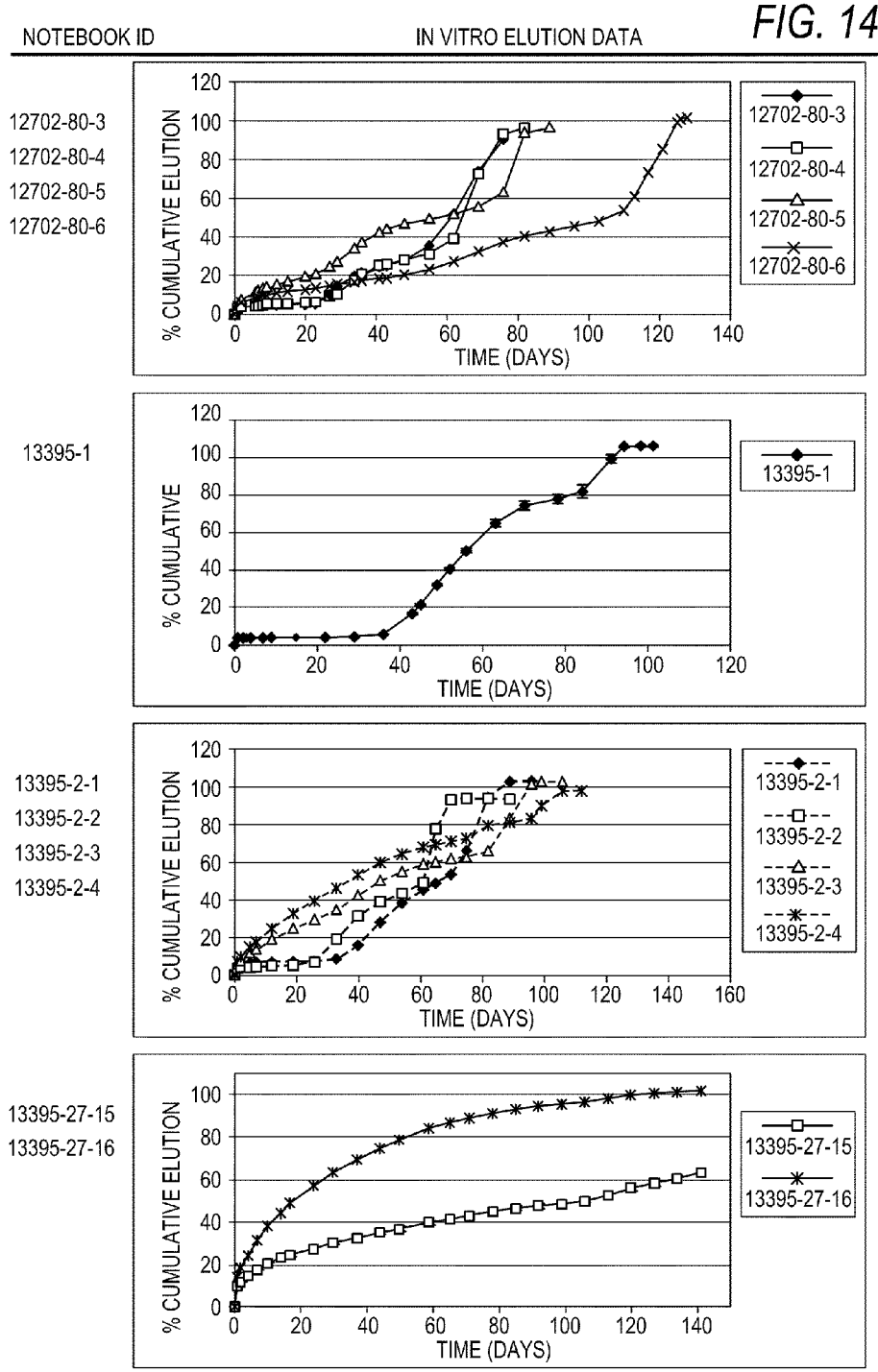
Figure 15:
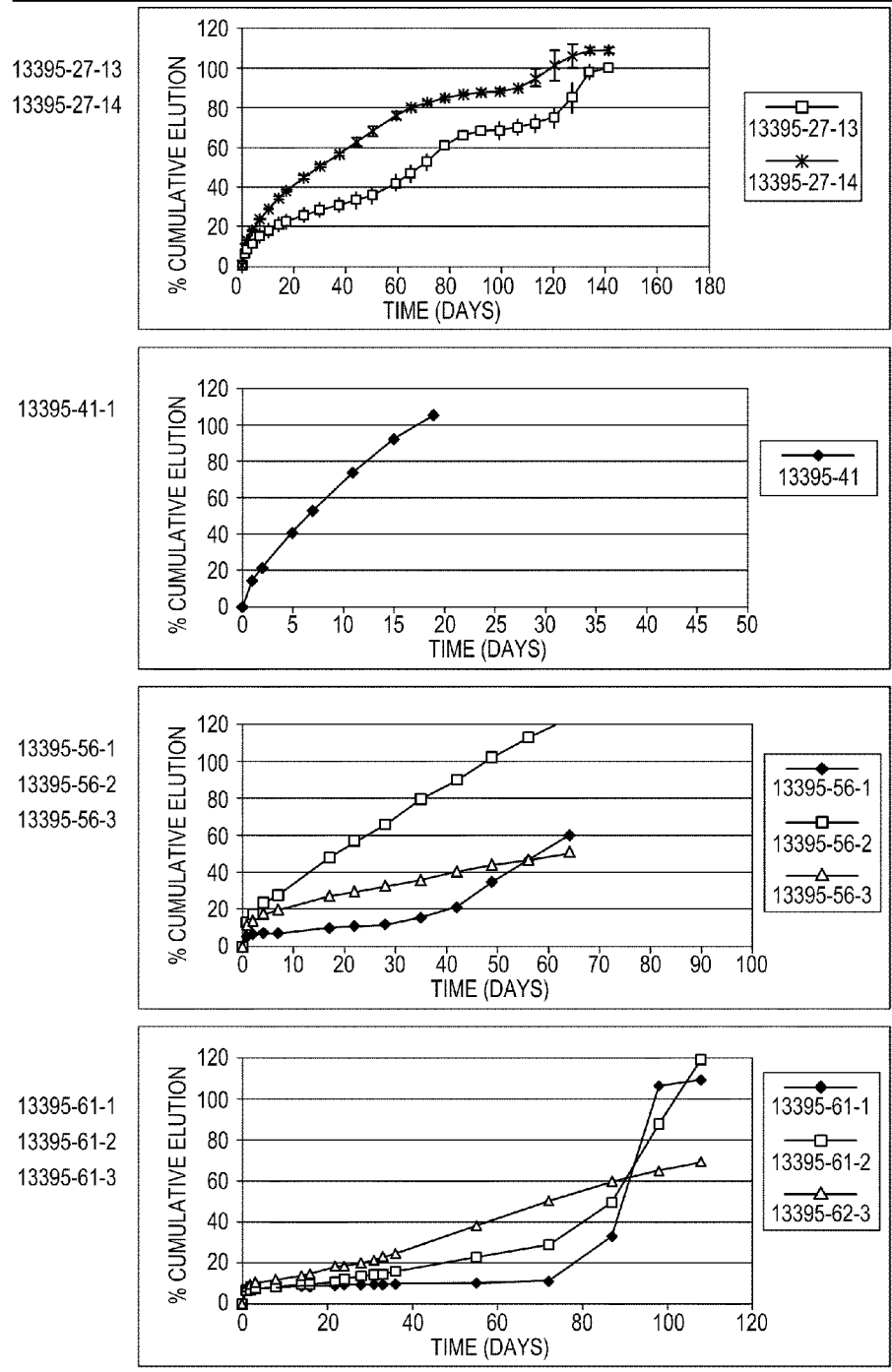
Figure 16:
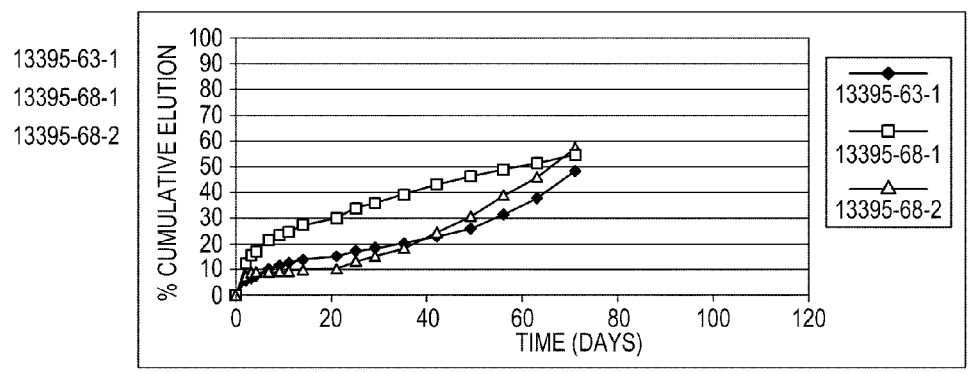

To date, the inventors have conducted the present study for a period of 57 days and have employed the following two tests: (1) the Hargreaves test on days 7, 14, 21, 28, 35, 42, 49, and 56; and (2) the von Frey test on days 8, 15, 22, 29, 36, 43, 50, and 57. The results of theses tests are summarized in FIGS. 3-6 and show the efficacy of sulindac of the recited time periods. These results are summarized in FIGS. 3 and 4.

The pain behavioral response (measured as a percentage of baseline) for thermal hyperalgesia (FIG. 3) indicates that sulindac delivered intraperitoneally at 0.4 mg/kg/day consistently reduced the behavioral response when compared to unloaded polymer depot (85/15 PLGA Control). All six sulindac-loaded polymer depots were able to reduce pain behavioral responses, at least for one time point, when compared to unloaded depot. Most of the formulation experienced a drop in efficacy at some point after the initial burst of drug at implantation; however, the 27% 85/15 PLGA and 25% DL-PLA formulations took a few weeks to reduce pain at all.

The pain behavioral response (measured as a percentage of baseline) for mechanical allodynia indicates that sulindac delivered intraperitoneally at 0.4 mg/kg/day reduced the behavioral response when compared to unloaded polymer depots (85/15 PLGA Control). All six sulindac-loaded polymer depots were able to reduce pain behavioral responses when compared to unloaded depot; although, each formulation took a few weeks to demonstrate this effect.

These results show that sulindac at the different drug loads can reduce, prevent, or treat pain for time periods beyond 57 days.

Example 3

Purpose: The purpose of these studies were to evaluate the in vivo drug elution rate from a biodegradable polymer dosage form and compare it to previously generated in vitro data.

Study 1:

Experimental Methods Summary: Seventy rats were utilized in this study. One group used obese rats to determine how the drug release differs from normal tissue versus fatty tissue. Every rat was implanted with subcutaneous (SQ) implants. All rats implanted with active polymer (drug containing) received two active implants and one vehicle only implant between the two active implants. The two active implants were implanted to the left of the dorsal midline while the polymer only (control) was implanted in between the active implants and to the right of the dorsal midline. The six rats receiving vehicle only also received three (3) implants. These vehicle-only rats were allowed for the determination of local reaction to the polymer at 2, 4, and 8 weeks in the absence of any systemic level of sulindac, which could reduce inflammatory responses. The polymer pellets were implanted by, first, making a dorsal midline skin incision and creating a lateral SQ pocket by blunt dissection. The pellets were deposited with an open-ended syringe. The skin incision was closed using skin staples. The implant sites were demarcated (on the opposite side of midline that the implant is injected) with a line using a tattoo machine. The rats were recovered after implant and sacrificed at various pre-determined timepoints. At necropsy, the remaining dosage form was identified and some portion of it was recovered. The retrieved portion of the dosage form was weighed and analyzed for drug content. At termination, a blood sample was collected via cardiac puncture and serum was isolated for further drug analysis.

| | | Number Of Animals Sacrificed | | | | | Total Number of |
|---|---|---|---|---|---|---|---|
| Group | Dosage Form | Day 3 | Week 1 | Week 2 | Week 3 | Week 4 | Week 8 | Animals |
| 1 | 0% drug load | 0 | 0 | 2 | 0 | 2 | 2 | 6 |
| 2 | 20% drug load | 3 | 2 | 3 | 2 | 3 | 3 | 16 |
| 3 | 25% drug load | 3 | 2 | 3 | 2 | 3 | 3 | 16 |
| 4 | 30% drug load | 3 | 2 | 3 | 2 | 3 | 3 | 16 |
| 5* | 25% drug load | 3 | 2 | 3 | 2 | 3 | 3 | 16 |

Drug = small molecule COX inhibitor, sulindac
*Group contained 16 obese rats that received the mid-range formulation Study 2:
Experimental Methods Summary: Eighty four rats were utilized in this study. Group 2 used Zucker (genetically obese) rats to determine how the drug release differs in normal tissue vs. fatty tissue. The Zucker rats received implants at two sites. The first implant site was at the base of the neck approximately 3 cm off the dorsal midline. The second implant site was implanted on the flank just cranial to the rear leg.

All remaining groups used Sprague Dawley rats. Every rat was implanted with two or three subcutaneous (SQ) implants (2 sites per animal). Each Group (1-4) received different formulations of active-loaded polymers. Groups 8-10 received formulations of unloaded (control) polymer (3 sites per animal).

The polymer pellets were implanted by making a dorsal midline skin incision (approximately 2 cm long) and creating a lateral SQ pocket (approximately 1 cm×1 cm) by blunt dissection. The pellets were deposited with forceps. The skin incision was closed using skin staples. The rats were allowed to recover from the implant procedure, and sacrificed on Days 3, 7, 14, 21, 28, and 66 according to a predetermined schedule. At necropsy, the remaining dosage form was identified, and some portion was recovered. The retrieved portion of the dosage form was weighed and analyzed for drug content. At termination, a blood sample was collected via cardiac puncture (approximately 1 mL) and transferred to an EDTA tube. Plasma in EDTA was isolated for future drug analysis.

| Gr | Strain of Rat | Formul. ID | Dosage Form | Pellet Number | Pellet Dimension (L × D) (mm) | # of Test Sites per Rat | Number of Sacrifices | Animal Sacrifices[a] | Total # of Rats |
|---|---|---|---|---|---|---|---|---|---|
| 1 | N | 13395-63-1 | 20% sulindac in 85/15 PLGA + 10% mPEG | 6 | 4 × 0.75 | 2 | 6 | 3 | 18 |
| 2 | Z | 13395-63-1 | 20% sulindac in 85/15 PLGA + 10% mPEG | 6 | 4 × 0.75 | 2 | 6 | 3 | 18 |
| 3 | N | 13395-68-1 | 25% sulindac in 85/15 PLGA + 10% mPEG | 6 | 4 × 0.75 | 2 | 6 | 3 | 18 |
| 4 | N | 13395-68-2 | 25% sulindac in DL-PLA | 6 | 4 × 0.75 | 2 | 6 | 3 | 18 |
| 5 | N | 13395-68-5 | 85/15 PLGA + 10% mPEG | 6 | 4 × 0.75 | 3 | 2 | 3 | 6 |
| 6 | N | 13395-68-4 | DL-PLA | 5 | 4 × 0.75 | 3 | 2 | 3 | 6 |

N = normal ~300 g Spague-Dawley
Z = Zucker rat (Crl: ZUC-lepr[fa]) obese strain
[a]Groups 1-4 was sacrificed at: 3, 7, 14, 21, 28, and 56 days post-implant (Implant = Day 0)
Groups 5-6 was sacrificed at: 28 and 56 days post-implant (Implant = Day 0)

Five of each of the sulindac formulations were made and are shown in Table 5.

| | IVIVC-1 Study Table 5 Sulindac Content Purity and Results (n = 5) | | | | | |
|---|---|---|---|---|---|---|
| Formulation | Ave Pellet Wt. (mg) | Drug Content mg/pellet | Content Uniformity | % Drug Load | % Theoretical | Drug Purity % Peak Area |
| 20% drug PLGA 8515 10% mPEG | 0.583 | 0.114 | 13.6% | 19.6% | 98.2% | 99.97% |
| 25% drug PLGA 8515 | 0.400 | 0.098 | 8.6% | 24.6% | 98.5% | 100% |

-continued

| | IVIVC-1 Study Table 5 Sulindac Content Purity and Results (n = 5) | | | | | |
|---|---|---|---|---|---|---|
| Formulation | Ave Pellet Wt. (mg) | Drug Content mg/pellet | Content Uniformity | % Drug Load | % Theoretical | Drug Purity % Peak Area |
| 10% mPEG 30% drug PLGA 8515 10% mPEG | 0.539 | 0.158 | 16.2% | 29.3% | 97.8% | 99.89% |

Figure 19:
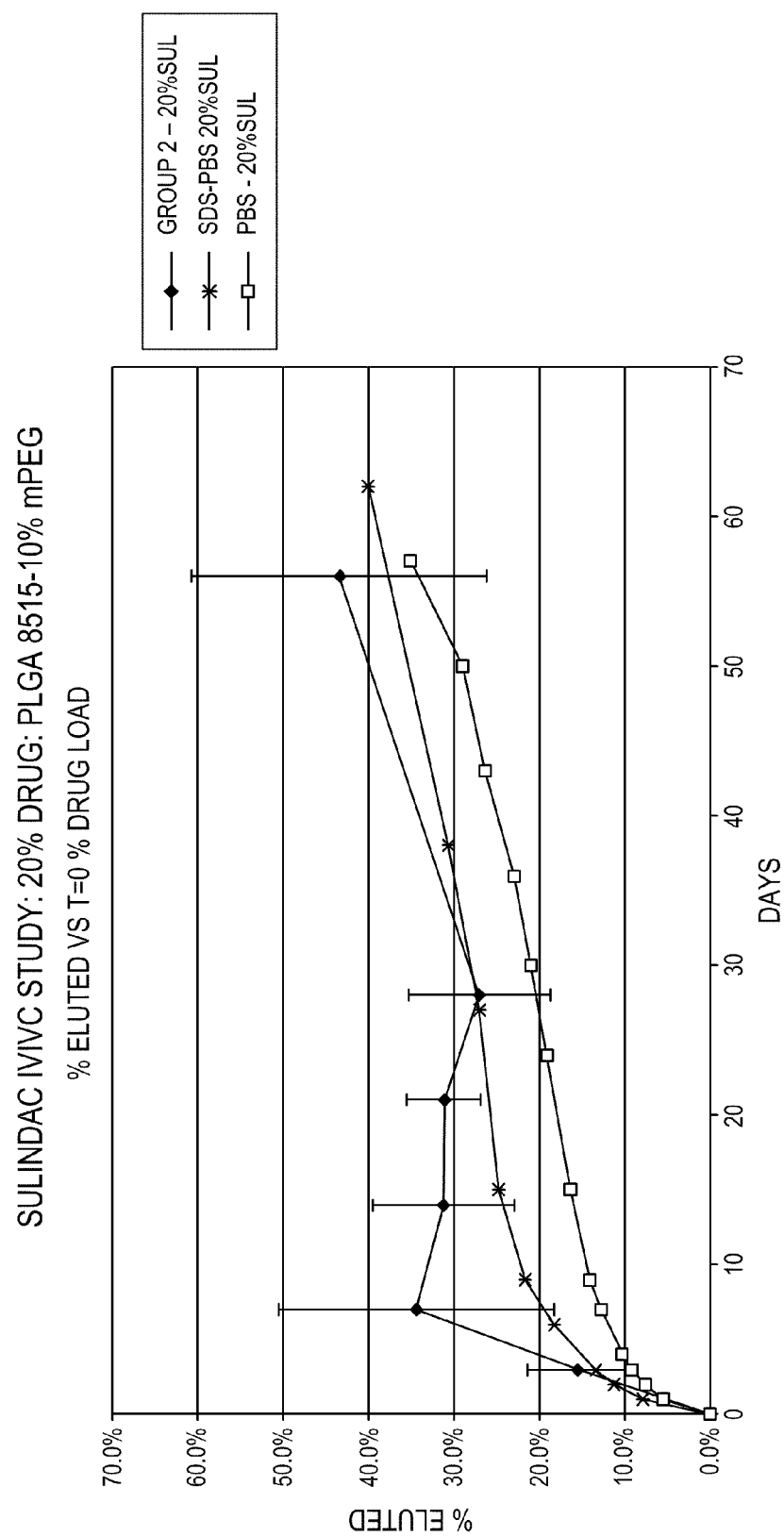
FIGS. 19-25 show in vitro elution vs in vivo elution profiles for exemplary sulindac formulations.
Figure 20:
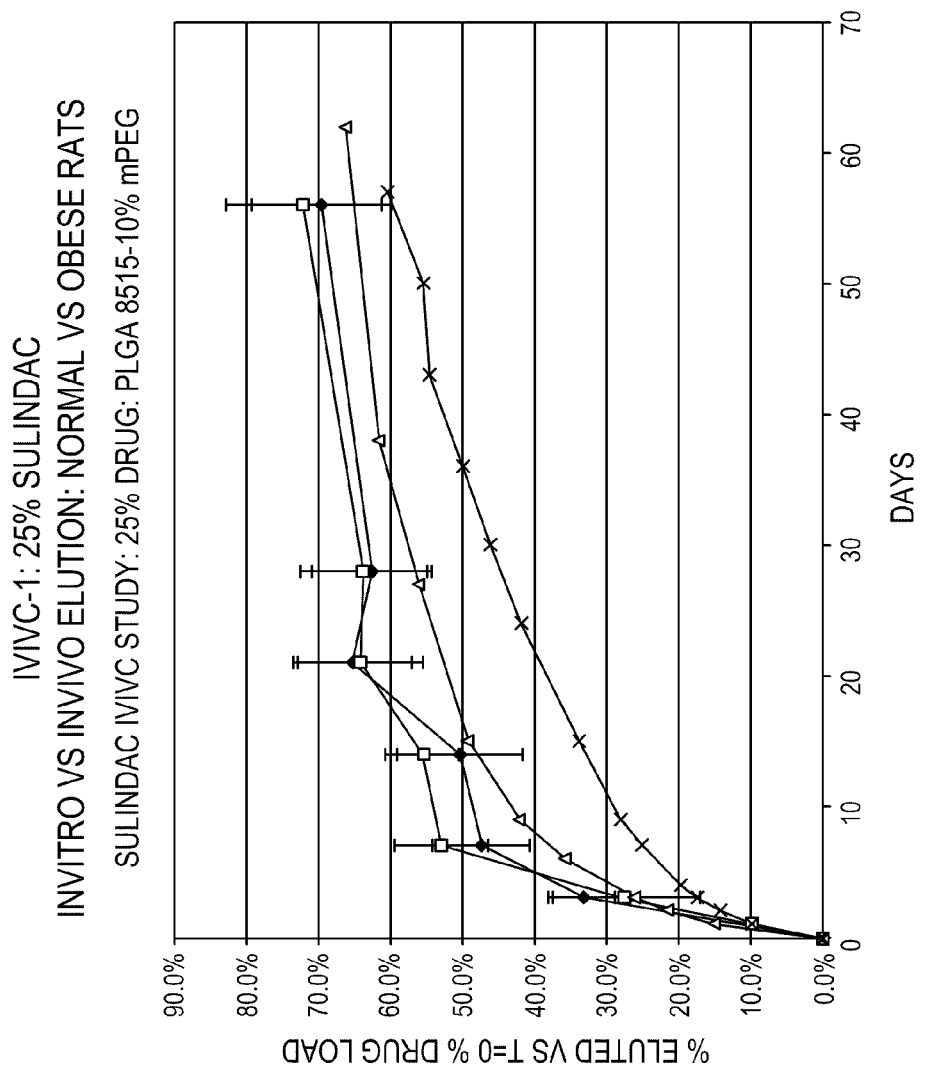
Figure 21:
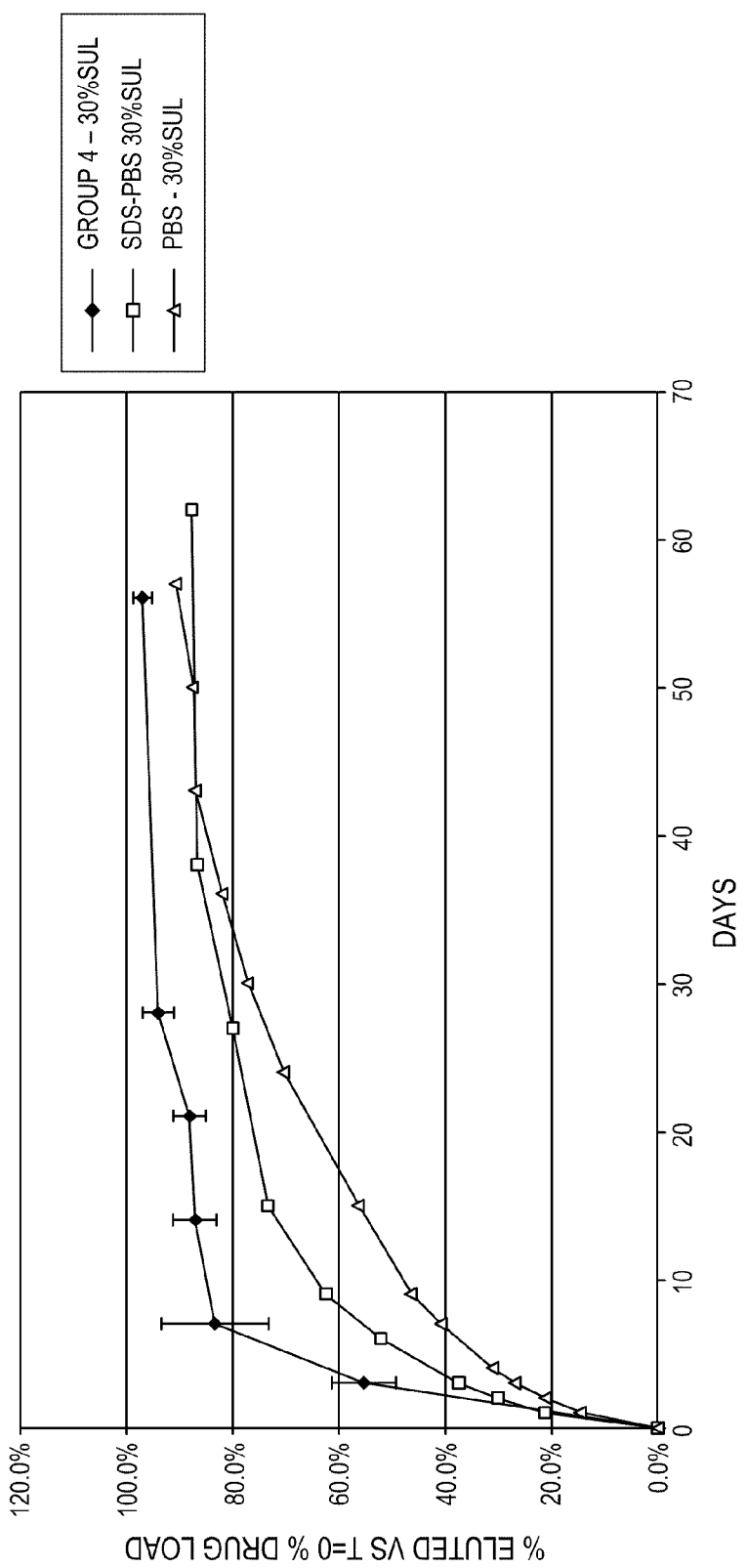

The elution profiles for each formulation in vivo vs in vitro are shown in FIG. 19-21. The sulindac load was increased starting at 20 wt %, 25 wt % and 30 wt %. Each formulation released sulindac over about 55-65 days. In FIG. 19, drug depots loaded with 20% sulindac released about 35% to 45% of the drug, with some releasing for over 60 days. The in vitro data generally correlated with the in vivo data, where there was an initial burst of sulindac for the first 3 days and then a more consistent release for up to 60 days (PBS and PBS with SDS were used to measure in vitro elution). The in vivo elution data (Group 2) were obtained by explanting the drug depot and measuring the % drug left in the drug depot. Between 30% to 40% of the drug was eluted after the initial burst period of about 3 days.

In FIG. 20, drug depots loaded with 25% sulindac. The release rate was higher with the 25% sulindac load compared to the 20% sulindac load (in FIG. 19). There was an initial burst of sulindac within the first few days (10% to 20% release). The in vitro data generally correlated with the in vivo data, where there was an initial burst of sulindac for the first 3 days and then a more consistent release for up to 60 days (PBS and PBS with SDS were used to measure in vitro elution). 60% to 70% of the sulindac eluted from the drug depot at the end of 55-65 days. The in vivo elution data (Groups 3 and 5) were obtained by explanting the drug depot and measuring the % drug left in the drug depot. Between about 50% to about 70% of the drug was eluted at the end of 55 days after the initial burst period of about 3 days.

In FIG. 21, a higher drug load of 30% sulindac was used in the drug depot. The drug depot with 30% sulindac load released about 85% to 98% of the drug from the drug depot after a period over 55 to over 60 days. The release profile remained approximately consistent after 20 days. There was an initial burst of sulindac (about 20% to about 55%) within the first few days. In summary, as the drug depot loads were increased from 20% to 30%, the % of total drug eluted increased to as high as 100% with drug loads up to 30%.

Figure 22:
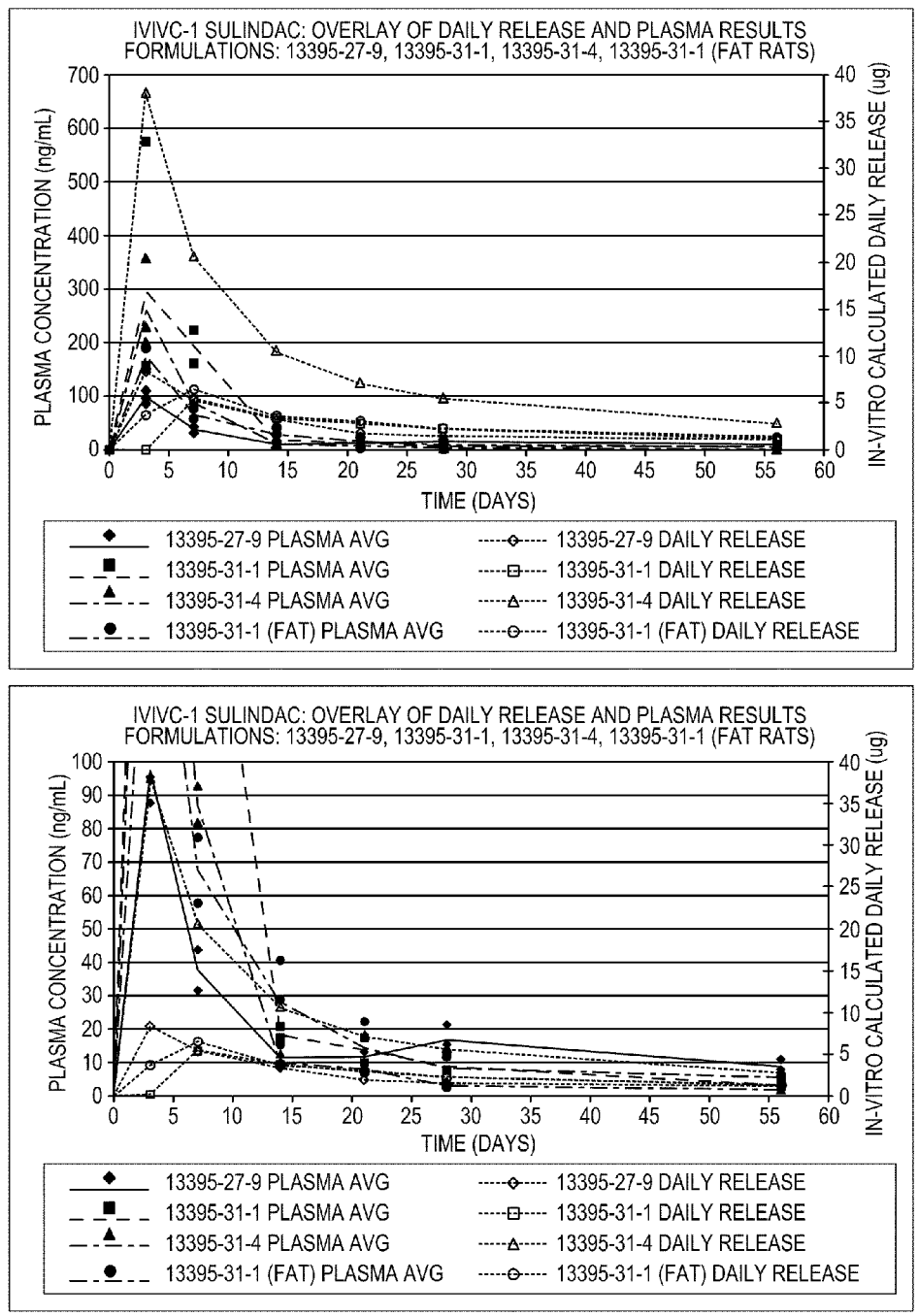

FIG. 22 shows in vivo plasma concentrations in obese rats and average weight rats and in vitro daily release profiles. The lower graph is an expanded view of the upper graph to show the lower plasma concentration ranges. Although 12 pellets were implanted (which is generally double the human dose (6 pellets are generally equivalent to the human dose), the plasma concentration of sulindac was relatively low. There was an initial burst within the first 4 days with Cmax between about 90 ng/ml and 300 ng/ml, then a relatively consistent release after day 12 for over 55 days. The in vitro daily release of sulindac was about 5 mcg to about 7 mcg/day from the drug depot. The release was for over 55 days. An initial burst effect where bolus doses as high as 40 mcg/day was seen for one of the formulations shown by the peaks in the first 3 days.

Example 4

The following formulations described in Table 6 were made.

| | IVIVC-2 Study Table 6 Sulindac Content Purity and Results Group 1: Sulindac 20%: 70% PLGA 8515: 10% mPEG | | | | | |
|---|---|---|---|---|---|---|
| Formulation | Ave Dose Wt. 6 Pellets (mg) | Drug Content mcg/pellet | Content Uniformity | % Drug Load | % Theoretical | Drug Purity % Peak Area |
| Pre-Sterile | 15.25 | 2919 | 6.5% | 19.1% | 95.6% | 99.5% |
| Post-Gamma | 15.34 | 2956 | 2.1% | 19.3% | 96.3% | 99.6% |

Figure 23:
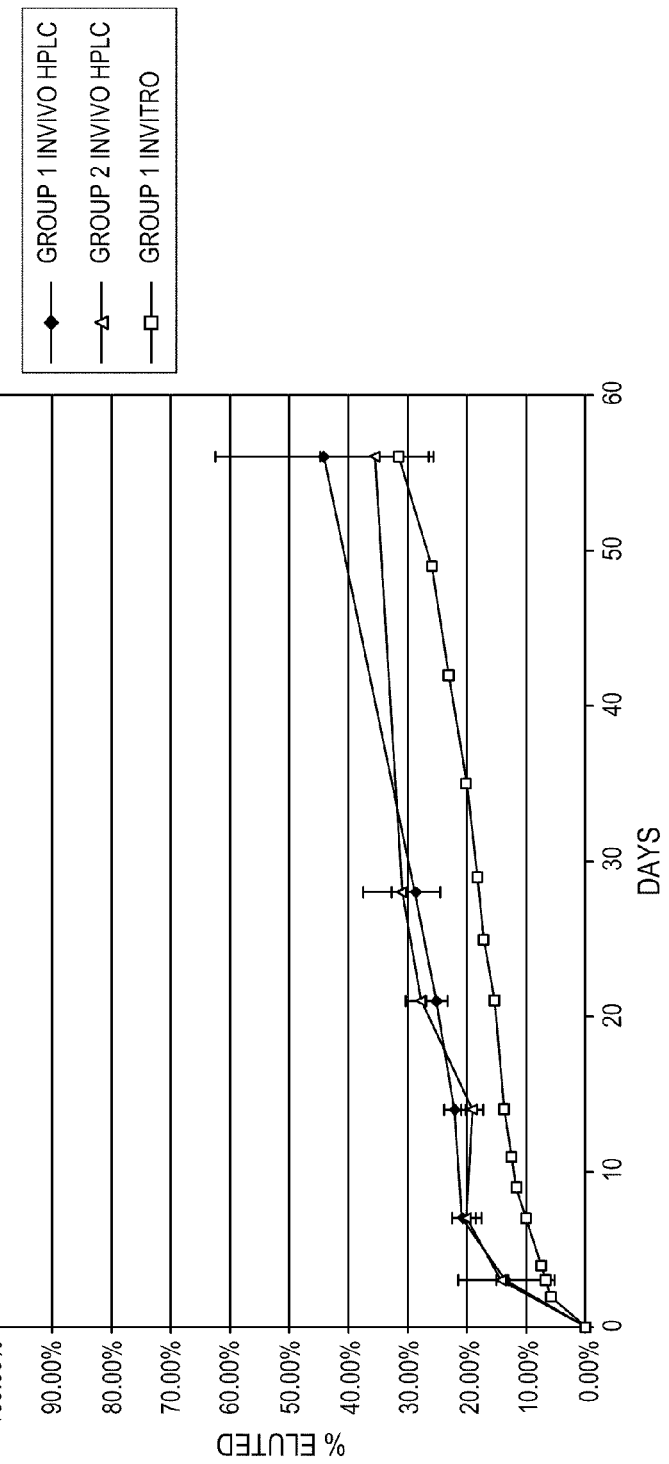

The elution profiles in vivo vs in vitro are shown in FIG. 23. The sulindac load in the drug depot was 20 wt %. Each formulation released sulindac over about 57 days. In FIG. 23, drug depots loaded with 20% sulindac released about 10% to 20% of the drug in the first few days and then about 30% to 45% of the drug for about 57 days. The in vitro data generally correlated with the in vivo data, where there was an initial burst of sulindac for the first 3 days and then a more consistent release for up to 57 days (PBS and PBS with SDS were used to measure in vitro elution). The in vivo elution data (Groups 1 and 2) were obtained by explanting the drug depot and measuring the % drug left in the drug depot. Between 35% to 45% of the drug was eluted after 55 days.

Example 5

The following formulations described in Table 7 were made.

IVIVC-2 Study Table 7 Sulindac Content Purity and Results
Group 3: Sulindac 25%: 65% DL-PLA: 10% mPEG

| Formulation | Ave Dose Wt. 6 Pellets (mg) | Drug Content mcg/pellet | Content Uniformity | % Drug Load | % Theoretical | Drug Purity % Peak Area |
|---|---|---|---|---|---|---|
| Pre-Sterile | 15.25 | 2919 | 6.5% | 19.1% | 95.6% | 99.5% |
| Post-Gamma | 15.34 | 2956 | 2.1% | 19.3% | 96.3% | 99.6% |

IVIVC-2 Study Table 8 Sulindac Content Purity and Results
Group 4: Sulindac 25%: 75% DL-PLA

| Formulation | Ave Dose Wt. 6 Pellets (mg) | Drug Content mcg/pellet | Content Uniformity | % Drug Load | % Theoretical | Drug Purity % Peak Area |
|---|---|---|---|---|---|---|
| Pre-Sterile | 13.63 | 3295 | 2.4% | 24.2% | 96.7% | 99.5% |
| Post-Gamma | 13.91 | 3366 | 4.1% | 24.2% | 96.8% | 98.9% |

Figure 24:
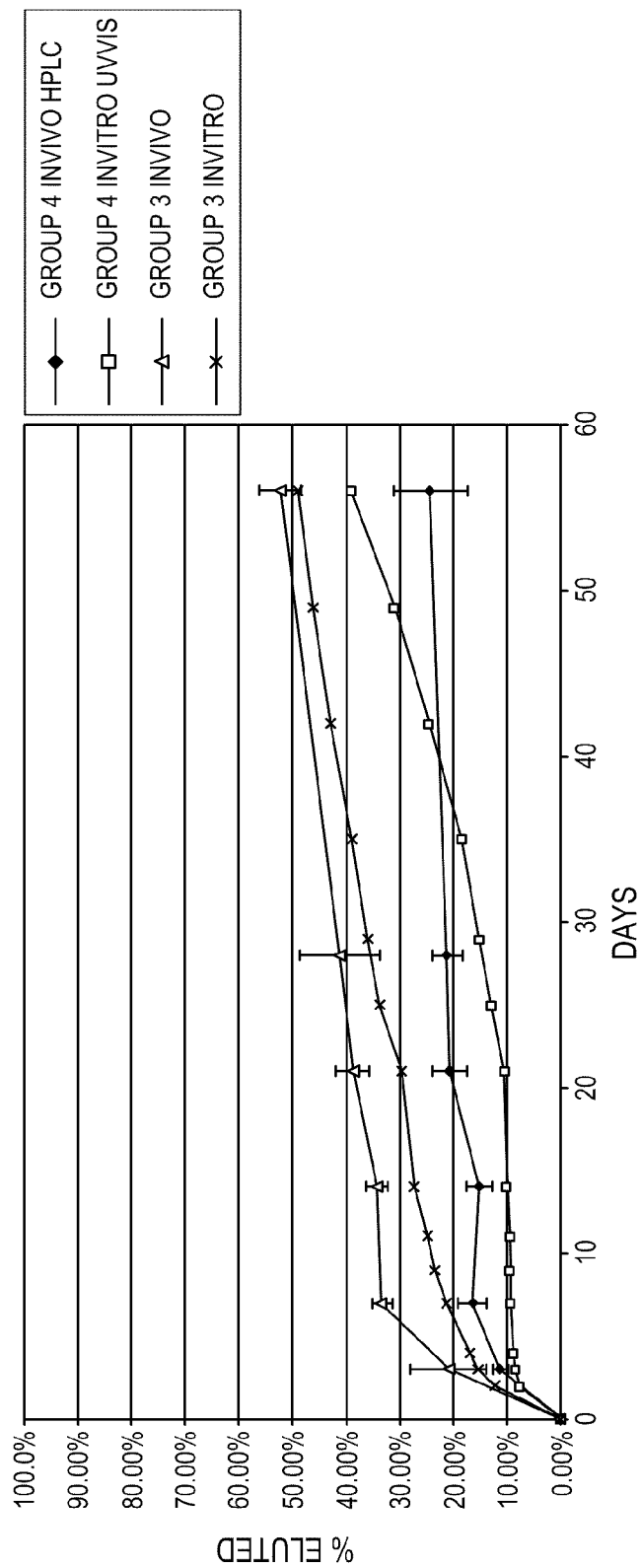

The elution profiles for Tables 7 and 8 are shown in FIG. 24. The sulindac drug depot had an initial burst effect of between 10 to 20% of the dose eluted on a daily basis in the first three days with steady consistent release of the sulindac occurring after about day 5. Between 20% and 50% of the sulindac was eluted from the depot after about 55 days. The in vivo elution data (Groups 3 and 4) were obtained by explanting the drug depot from the rat and measuring the % drug left in the drug depot. Between about 50% to 55% of the drug was eluted from the drug depot after 55 days.

Figure 25:
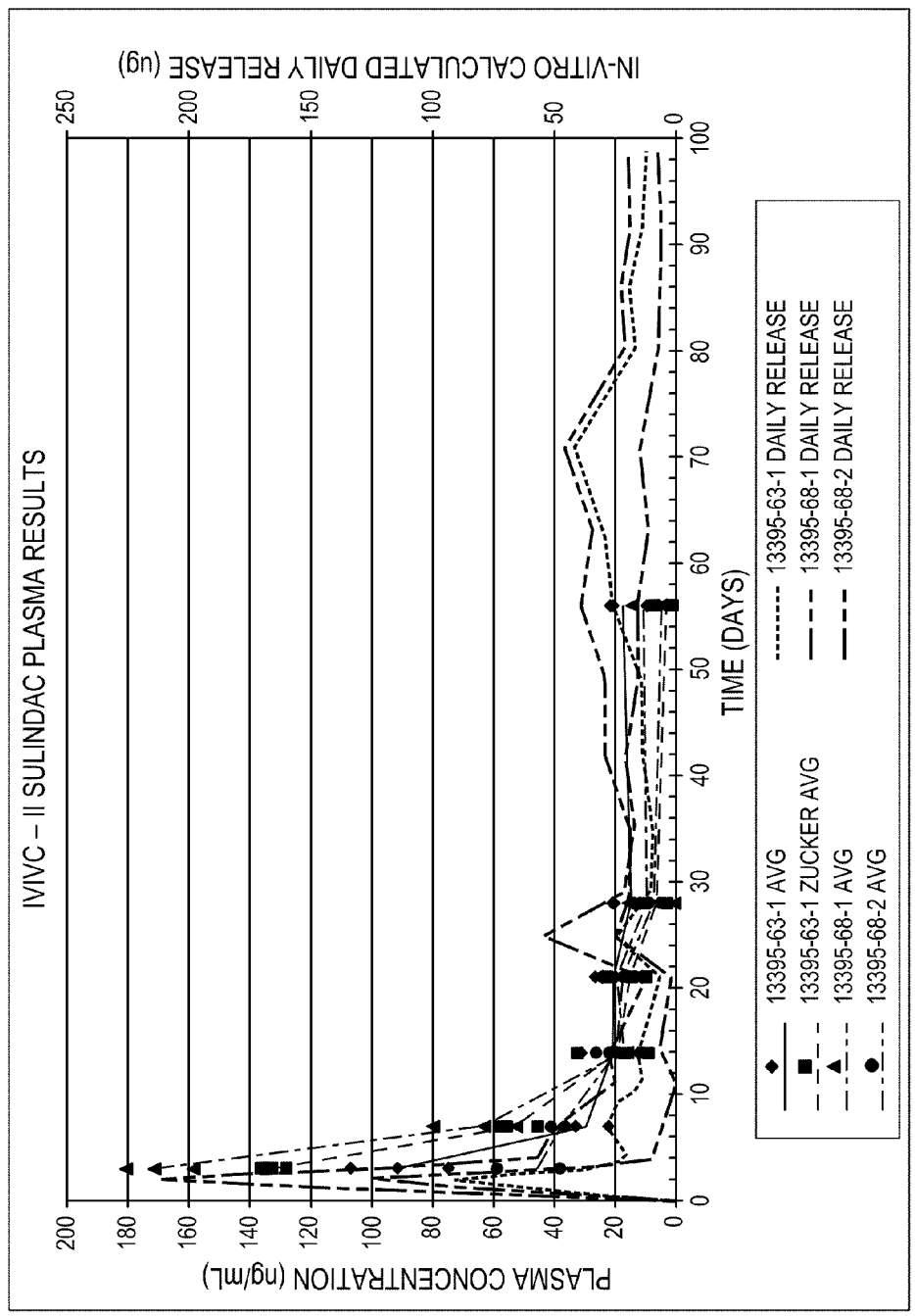

FIG. 25 shows in vivo plasma concentrations in obese rats and average weight rats and in vitro daily release profiles. Although 12 pellets were implanted (which is generally double the human dose (6 pellets are generally equivalent to the human dose), the plasma concentration of sulindac was relatively low. There was an initial burst within the first 3 days with Cmax between about 40 ng/ml and 180 ng/ml, then a relatively consistent release after day 12 for over 55 days. The in vitro daily release of sulindac was about 5 mcg to about 40 mcg/day from the drug depot. The release was for over 100 days. An initial burst effect where bolus doses as high as 210 mcg/day was seen for one of the formulations shown by the peaks in the first 3 days.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An implantable drug depot for reducing or treating pain and/or inflammation in a patient in need of such treatment, the implantable drug depot comprising sulindac or a pharmaceutically acceptable salt thereof in an amount from about 20 wt. % to about 40 wt. % based on the weight of the drug depot, and at least one biodegradable polymer comprising poly (lactic-co-glycolic acid) capable of releasing the sulindac or a pharmaceutically acceptable salt thereof for at least 3 days, wherein the at least one biodegradable polymer has an inherent viscosity of from 0.45 dL/g to 0.8 dL/g and the drug depot has a surface that releases a burst dose of sulindac or a pharmaceutically acceptable salt thereof in an amount of 10% to 20% by weight based on the total weight of the sulindac or pharmaceutically acceptable salt thereof in the drug depot within 72 hours and the drug depot comprises an adherent gel that stiffens after delivery to a target site having a pre-dosed modulus of elasticity of about $5 \times 10^{-4}$ dynes/cm$^2$ to about $1 \times 10^5$ dynes/cm$^2$ and a post-dosed modulus of elasticity in the range of about $2 \times 10^5$ dynes/cm$^2$ to about $5 \times 10^5$ dynes/cm$^2$ and the drug depot comprises magnesium carbonate, and the drug depot further comprises a plasticizer comprising mPEG in an amount of from about 0.05 wt. % to about 20 wt. %.

2. An implantable drug depot according to claim 1, wherein said sulindac comprises about 25% wt. % of the drug depot, and the poly (lactic-co-glycolic acid) has a L/G ratio of 85:15.

3. An implantable drug depot according to claim 1, wherein said at least one biodegradable polymer comprises at least 60 wt. % of the drug depot.

4. An implantable drug depot according to claim 1, wherein said drug depot is used to reduce, or treat sciatic pain.

5. An implantable drug depot according to claim 1, wherein the poly(lactic-co-glycolic acid) comprises a mixture of polyglycolide and polylactide.

6. An implantable drug depot according to claim 5, wherein said mixture comprises more polylactide than polyglycolide and releases the sulindac or a pharmaceutically acceptable salt thereof over at least 3 to 180 days.

7. An implantable drug depot according to claim 1, wherein said sulindac comprises sulindac sodium.

8. An implantable drug depot according to claim 1, wherein the drug depot releases an effective amount of the sulindac or a pharmaceutically acceptable salt thereof over a period of at least 50 days.

9. An implantable drug depot for reducing, or treating pain and/or inflammation according to claim 1, wherein the at least one biodegradable polymer comprises at least 80 wt. % of said drug depot.

10. An implantable drug depot according to claim 1, wherein the depot has a length of from about 0.5 mm to 5 mm and a thickness of from about 0.005 to about 1.0 mm.

11. An implantable drug depot according to claim 1, wherein the magnesium carbonate is present in the depot in an amount of 0.05 wt. % to 20 wt. %.

12. An implantable drug depot according to claim 1, wherein the sulindac is released at a rate of 7 to 12 mg/day for at least 50 days and the depot further comprises particles of from about 10 micrometers to about 200 micrometers.

13. An implantable drug depot according to claim 1, wherein the drug depot comprises mPEG in an amount of 10 wt %.

14. An implantable drug depot for reducing or treating pain, and/or inflammation in a patient in need of such treatment, the implantable drug depot comprising sulindac or a pharmaceutically acceptable salt thereof in an amount of from about 20 wt. % to about 40 wt. % of the drug depot, and at least one polymer, wherein the at least one polymer comprises poly (lactic-co-glycolic acid) and said drug depot comprises magnesium carbonate and is capable of releasing the sulindac or a pharmaceutically acceptable salt thereof over a period of at least 3 days, wherein the at least one biodegradable polymer has an inherent viscosity of from 0.45 dL/g to 0.8 dL/g and the drug depot has a surface that releases a burst dose of sulindac or a pharmaceutically acceptable salt thereof in an amount of 10% to 20% by weight based on the total weight of the sulindac or a pharmaceutically acceptable salt thereof in the drug depot within 72 hours and the drug depot comprises an adherent gel that stiffens after delivery to the target site having a pre-dosed modulus of elasticity of from about $5 \times 10^4$ dynes/cm$^2$ to about $1 \times 10^5$ dynes/cm$^2$ and a post-dosed modulus of elasticity in the range of about $2 \times 10^5$ dynes/cm$^2$ to about $5 \times 10^5$ dynes/cm$^2$, and the drug depot further comprises a plasticizer comprising mPEG in an amount of from about 0.05 wt. % to about 20wt. %.

15. A method for reducing, or treating pain and/or inflammation, wherein said method comprises implanting the drug depot according to claim 1 in a patient in need of such treatment to reduce or treat pain and/or inflammation.

16. A method according to claim 15, wherein said sulindac or a pharmaceutically acceptable salt thereof comprises from about 5 wt. % to about 15 wt. % of the drug depot.

17. A method according to claim 15, wherein said biodegradable polymer comprises at least 60 wt. % of the drug depot.

18. A method according to claim 15, wherein the at least one biodegradable polymer further comprises one or more of poly(lactide-co-glycolide), poly(orthoester), polylactide, polyglycolide, D-lactide, L-lactide, D,L-lactide, D,L-lactide-caprolactone, glycolide-caprolactone D,L-lactide-glycolide-caprolactone or a combination thereof.

19. A method according to claim 18, wherein the at least one biodegradable polymer further comprises poly(lactic-co-glycolic acid) and said poly(lactic-co-glycolic acid) comprises a mixture of polyglycolide and polylactide.

20. A method according to claim 19, wherein said mixture comprises more polylactide than polyglycolide.

21. A method according to claim 15, wherein said sulindac comprises sulindac sodium.

22. A method according to claim 15, wherein one or more drug depots are implanted at a plurality of sites that triangulate a pain generator.

23. A method of making an implantable drug depot of claim 1, the method comprising combining a biocompatible polymer and a therapeutically effective amount of the sulindac or a pharmaceutically acceptable salt thereof and forming the implantable drug depot from the combination.

* * * * *

UNITED STATES PATENT AND TRADEMARK OFFICE
CERTIFICATE OF CORRECTION

PATENT NO. : 9,289,409 B2  Page 1 of 2
APPLICATION NO. : 12/413236
DATED : March 22, 2016
INVENTOR(S) : Zanella et al.

It is certified that error appears in the above-identified patent and that said Letters Patent is hereby corrected as shown below:

On the Title Page

Item (75), under "Inventors", in Column 1, Line 2, delete "Vanja M King," and insert -- Vanja M. King, --, therefor.

Item (75), under "Inventors", in Column 1, Line 3, delete "Christopher M Hobot," and insert -- Christopher M. Hobot, --, therefor.

Item (75), under "Inventors", in Column 1, Line 4, delete "S Mark" and insert -- S. Mark --, therefor.

Item (75), under "Inventors", in Column 1, Line 8, delete "F McKay," and insert -- F. McKay, --, therefor.

Item (75), under "Inventors", in Column 1, Line 8, delete "Kathy L" and insert -- Kathy L. --, therefor.

Item (56), under "OTHER PUBLICATIONS", in Column 2, Line 3, delete "www.ciltinc.com," and insert -- www.qltinc.com, --, therefor.

In the Specification

In Column 8, Line 44, delete "fuoric," and insert -- fluoric, --, therefor.

In Column 8, Line 60, delete "bescylate," and insert -- besylate, --, therefor.

In Column 9, Line 11, delete "basilicimab)," and insert -- basiliximab), --, therefor.

In Column 9, Line 46, delete "pyridinylamino)" and insert -- pyridinylamino --, therefor.

In Column 9, Line 57, delete "bupivicaine," and insert -- bupivacaine, --, therefor.

Signed and Sealed this
Thirty-first Day of May, 2016

Michelle K. Lee
*Director of the United States Patent and Trademark Office*

CERTIFICATE OF CORRECTION (continued)
U.S. Pat. No. 9,289,409 B2

In the Specification

In Column 9, Line 61, delete "mepiridine," and insert -- meperidine, --, therefor.

In Column 10, Line 15, delete "dexmetdetomidine," and insert -- dexmedetomidine, --, therefor.

In Column 11, Line 12, delete "polyphosphagenes," and insert -- polyphosphazenes, --, therefor.

In Column 11, Line 27, delete "D-Sorbital, maltodextran," and insert -- D-Sorbitol, maltodextrin, --, therefor.

In Column 14, Line 38, delete "pyrolidone," and insert -- pyrrolidone, --, therefor.

In Column 17, Line 35, delete "interparenchymal" and insert -- intraparenchymal --, therefor.

In Column 23, Line 47, delete "was" and insert -- way --, therefor.

In Column 24, Line 67, delete "does" and insert -- dose --, therefor.

In Column 25, Line 7, delete "does" and insert -- dose --, therefor.

In Column 26, Line 59, delete "☐L 7E" and insert -- DL 7E --, therefor.

In Column 26, Line 63, delete "shows" and insert -- show --, therefor.

In Column 27, Line 46, delete "theses" and insert -- these --, therefor.

In Columns 29 & 30, in Table, in Line 2, delete "Dimension" and insert -- Dimensions --, therefor.

In the Claims

In Column 34, Line 44, in Claim 2, delete "25% wt. %" and insert -- 25 wt. % --, therefor.

In Column 34, Line 50, in Claim 4, delete "reduce, or" and insert -- reduce or --, therefor.

In Column 35, Line 3, in Claim 10, delete "0.005" and insert -- 0.005 mm --, therefor.

In Column 36, Line 2, in Claim 14, delete "20wt. %." and insert -- 20 wt. %. --, therefor.

In Column 36, Line 16, in Claim 18, delete "glycolide-caprolactone" and insert -- glycolide-caprolactone, --, therefor.